United States Patent
Salhia

(10) Patent No.: US 11,035,849 B2
(45) Date of Patent: Jun. 15, 2021

(54) PREDICTING THE OCCURRENCE OF METASTATIC CANCER USING EPIGENOMIC BIOMARKERS AND NON-INVASIVE METHODOLOGIES

(71) Applicant: THE TRANSLATIONAL GENOMICS RESEARCH INSTITUTE, Phoenix, AZ (US)

(72) Inventor: Bodour Salhia, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 20 days.

(21) Appl. No.: 15/566,174

(22) PCT Filed: Apr. 12, 2016

(86) PCT No.: PCT/US2016/027087
§ 371 (c)(1),
(2) Date: Oct. 12, 2017

(87) PCT Pub. No.: WO2016/168174
PCT Pub. Date: Oct. 20, 2016

(65) Prior Publication Data
US 2018/0113116 A1 Apr. 26, 2018

Related U.S. Application Data

(60) Provisional application No. 62/146,516, filed on Apr. 13, 2015, provisional application No. 62/216,477, filed on Sep. 10, 2015.

(51) Int. Cl.
| | | |
|---|---|---|
| *C12Q 1/68* | (2018.01) | |
| *C07H 21/04* | (2006.01) | |
| *G01N 33/50* | (2006.01) | |
| *C12Q 1/6886* | (2018.01) | |

(52) U.S. Cl.
CPC ....... *G01N 33/5011* (2013.01); *C12Q 1/6886* (2013.01); *G01N 33/5091* (2013.01); *C12Q 2600/106* (2013.01); *C12Q 2600/118* (2013.01); *C12Q 2600/154* (2013.01); *C12Q 2600/158* (2013.01); *G01N 2800/52* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,883,202 A | 11/1989 | Wahl | |
| 5,130,238 A | 7/1992 | Malek et al. | |
| 5,210,015 A | 5/1993 | Gefland et al. | |
| 5,487,792 A | 1/1996 | King et al. | |
| 5,804,375 A | 9/1998 | Gefland et al. | |
| 5,925,517 A | 7/1999 | Tyagi et al. | |
| 6,214,979 B1 | 4/2001 | Gefland et al. | |
| 7,276,228 B2 | 10/2007 | DiMartino | |
| 2007/0105792 A1 | 5/2007 | DiMartino et al. | |
| 2008/0175814 A1 | 7/2008 | Phiasivongsa et al. | |
| 2012/0148561 A1 | 6/2012 | Hoon et al. | |
| 2012/0263654 A1 | 10/2012 | Morgan et al. | |
| 2013/0244885 A1 | 9/2013 | Wang et al. | |
| 2014/0045915 A1 | 2/2014 | Skog et al. | |
| 2015/0094222 A1* | 4/2015 | Sukumar | C12Q 1/6886 506/9 |

FOREIGN PATENT DOCUMENTS

| | | |
|---|---|---|
| EP | 0500244 A2 | 8/1992 |
| WO | 2001086001 A1 | 11/2001 |

OTHER PUBLICATIONS

Salhai et al. (PLOS One, vol. 9, No. 1, e85448, Jan. 2014). (Year: 2014).*
Nagata et al. (Oncotarget, vol. 8, No. 23, p. 37740-37750, 2017) (Year: 2017).*
Massie et al. (J. of Steroid Biochemistry & Molecular Biology, vol. 166, pp. 1-15, 2017) (Year: 2017).*
Wang et al., "Association of Promoter Methylation of RUNX# Gene with the Development of Esophageal Cancer: A Meta Analysis," PLoS One, Sep. 17, 2014, vol. 9, Iss. 9, pp. 107.
Kievits, T. et al. NASBA isothermal enzymatic in vitro nucleic acid amplification optimized for the diagnosis of HIV-1 infection. J. Virol Methods 1991; 35(3): 273-286.
Giachetti, C., et al. Highly sensitive multiplex assay for detection of human immunodeficiency virus type 1 and hepatitis C virus RNA. J Clin Microbiol 2002; 40(7): 2408-2419.
Walker, G.T., et al. Strand Displacement Amplification—an isothermal, in vitro DAN amplification technique. Nucleic Acids Res 1992; 20(7):1691-1696.
Tijssen. Chapter 2: Laboratory Techniques in Biochemistry and Molecular Biology—Hybridization with Nucleic Acid Probes, Part I:Theory and nucleic acid preparation; 1993 (Elsevier, N.Y.); vol. 24, Issue 24; pp. 20-78.
Ausubel, et al. Current Protocols in Molecular Biology. 2003, John Wiley & Sons, Inc.; Chapters 2, 4, 6 & 14.

(Continued)

*Primary Examiner* — Jeanine A Goldberg
(74) *Attorney, Agent, or Firm* — The Noblitt Group, PLLC

(57) ABSTRACT

The present technology provides a method of determining whether a subject with cancer is likely to experience one or more metastases. The method may include determining a methylation level of at least one gene selected from the group consisting of BEND4, CDH4, C1QL3, ERG, GP5, GSC, HTR1B, LMX1B, MCF2L2, PENK, REC8, RUNX3, PAX5, PCDHIO, SP8, SP9, STAC2, ULBP1, UNC13A, VIM, VWC2 in a subject-derived sample and then comparing the subject-derived methylation level determined in step a) with a normal control level obtained from a normal sample. Thereafter, the method may include correlating an increase of said subject-derived methylation level as compared to the normal control level to a diagnosis the subject as likely to experience one or more metastases.

7 Claims, 24 Drawing Sheets

(56) References Cited

OTHER PUBLICATIONS

Sambrook, et al. Molecular Cloning. A Laboratory Manual. 2 ed., 1989, Cold Spring Harbor Laboratory Press, Plainview, NY; Chapters 7, 9 & 11.
Legendre, C., et al. Whole Genome Bisulfite Sequencing of Cell-Free DNA Identifies Signature Associated with Metastatic Breast Cancer. Clinical Epigentics 2015; 7:100.
Chaffer, et al. A Perspective on Cancer Cell Metastasis. Science 2011; 331(6024):1559-1564.
Griffith, O. L., et al. Omic approaches to preventing or managing metastatic breast cancer. Breast cancer Research 2011; 13(6):230.
Weigelt, B., et al. Breast cancer metastasis: markers and models. Nature reviews. Cancer 2005; 5:591-602.
Yan, M., et al. High risk factors of brain metastases in 295 patients with advanced breast cancer. Chin Med J (Engl) 2013; 126(7):1269-1275.
Blanco, M. A., et al. Signaling pathways in breast cancer metastasis—novel insights from functional genomics. Breast Cancer Research 2011; 13(2):206.
Eroles, P., et al. Molecular biology in breast cancer: intrinsic subtypes and signaling pathways. Cancer Treat Rev 2012; 38(6):698-707.
Chan, K.C., et al. Noninvasive detection of cancer-associated genome-wide hypomethylation and copy number aberrations by plasma DNA bisulfite sequencing. Proceedings of the National Academy of Sciences of the United States of America 2013; 110(47):18761-18768.
Harrell, J. C., et al. Genomic analysis identifies unique signatures predictive of brain, lung, and liver relapse. Breast Cancer Res Treat 2012; 132(2):523-535.
Korshunova, Y., et al. Massively parallel bisulphite pyrosequencing reveals the molecular complexity of breast cancer-associated cytosine-methylation patterns obtained from tissue and serum DNA. Genome Res 2008; 18(1):9-29.
Gormally, E., et al. Circulating free DNA in plasma or serum as biomarker of carcinogenesis: practical aspects and biological significance. Mutat Res 2007; 635(2-3):105-117.
Gormally, E., et al. Amount of DNA in plasma and cancer risk: a prospective study. International Journal of Cancer 2004; 111(5):746-749.
Jung, K., et al. A. Cell-free DNA in the blood as a solid tumor biomarker—a critical appraisal of the literature. Clinica chimica acta 2010; 411(21-22):1611-1624.
Bryzgunova, O. L., et al. Efficacy of bisulfite modification and recovery of human genomic and circulating DNA using commercial kits. European Journal of Molecular Biology 2013; 1:1-8.
Lim, J. H., et al. Cell-free fetal DNA and cell-free total DNA levels in spontaneous abortion with fetal chromosomal aneuploidy. PloS one 2013; 8:e56787.
Liu, J. B., et al. Plasma DNA methylation of Wnt antagonists predicts recurrence of esophageal squamous cell carcinoma. World J Gastroenterol 2011; 17(44):4917-4921.
Lau, Q. C., et al. RUNX3 is frequently inactivated by dual mechanisms of protein mislocalization and promoter hypermethylation in breast cancer. Cancer Research 2006; 66:6512-6520.
Miyamoto, K., et al. Identification of 20 genes aberrantly methylated in human breast cancers. International journal of cancer 2005; 116:407-414.
Kornegoor, R., et al. Promoter hypermethylation in male breast cancer: analysis by multiplex ligation-dependent probe amplification. Breast cancer research 2012; 14(4):R101.
Salhia, B., et al. Integrated genomic and epigenomic analysis of breast cancer brain metastasis. PloS one 2017; 9: e85448.
Appolloni, I., et al. A cadherin switch underlies malignancy in high-grade gliomas. Oncogene 2015; 34(15):1991-2002.
Chung, J. H., et al. DNA methylation profile during multistage progression of pulmonary adenocarcinomas. Virchows Archiv 2011; 459:201-211.

Hartwell, K. A., et al. The Spemann organizer gene, Goosecoid, promotes tumor metastasis. Proceedings of the National Academy of Sciences of the United States of America 2006; 103(50):18969-18974.
Xue, T. C., et al. Goosecoid promotes the metastasis of hepatocellular carcinoma by modulating the epithelial-mesenchymal transition. PloS one 2014; 9:e109695.
Zhou, L., et al. Regulation of UHRF1 by miR-146a/b modulates gastric cancer invasion and metastasis. FASEB journal : official publication of the Federation of American Societies for Experimental Biology 2013; 27(12):4929-4939.
Jao, T. M., et al. Protocadherin 10 suppresses tumorigenesis and metastasis in colorectal cancer and its genetic loss predicts adverse prognosis. International journal of cancer 2014; 135(11):2593-2603.
Fackler., M. J., et al. Genome-wide methylation analysis identifies genes specific to breast cancer hormone receptor status and risk of recurrence. Cancer research 2011; 71(19):6195-6207.
Irahara, N., et al. Precision of pyrosequencing assay to measure LINE-1 methylation in colon cancer, normal colonic mucosa, and peripheral blood cells. J Mol Diagn 2010; 12(2):177-183.
Melnikov, A., et al. Differential methylation profile of ovarian cancer in tissues and plasma. J Mol Diagn 2009; 11(1):60-65.
Melnikov, A., et al. Methylation profile of circulating plasma DNA in patients with pancreatic cancer. Journal of surgical oncology 2009; 99:119-122.
Nakayama, G., et al. A highly sensitive method for the detection of p16 methylation in the serum of colorectal cancer patients. Anti-cancer Res 2007; 27(36):1459-1463.
Ostrow, K. L., et al. Molecular analysis of plasma DNA for the early detection of lung cancer by quantitative methylation-specific PCR. Clinical cancer research 2010; 16(13):3463-3472.
Hoque, M. O., et al. Detection of aberrant methylation of four genes in plasma DNA for the detection of breast cancer. J Clin Oncol 2006; 24(26):4262-4269.
Bastian, P. J., et al. CpG island hypermethylation profile in the serum of men with clinically localized and hormone refractory metastatic prostate cancer. J Urol 2008; 179(2):529-534.
Fackler, M. J., et al. Novel methylated biomarkers and a robust assay to detect circulating tumor DNA in metastatic breast cancer. Cancer research 2014; 74(8):2160-2170.
Fiegl, H., et al. Methylated NEUROD1 promoter is a marker for chemosensitivity in breast cancer. Clinical cancer research 2008; 14(11):3494-3502.
Fiegl, H., et al. Circulating Tumor-Specific DNA: A Marker for Monitoring Efficacy of Adjuvant Therapy in Cancer Patients. Cancer research 2005; 65(4):1141-1145.
Liggett, T. E., et al. Methylation patterns in cell-free plasma DNA reflect removal of the primary tumor and drug treatment of breast cancer patients. International journal of cancer 2011; 128(2):492-499.
Muller, H. M., et al. DNA Methylation in Serum of Breast Cancer Patients: An Independent Prognostic Marker. Cancer Research 2003; 63:7641-7645.
Krueger, F., et al. Bismark: a flexible aligner and methylation caller for Bisulfite-Seq applications. Bioinformatics 2011; 27(11):1571-1572.
Akalin, A., et al. methylKit: a comprehensive R package for the analysis of genome-wide DNA methylation profiles. Genome Biol 2012; 13(10):R87.
Dawson, S. J., et al. Analysis of circulating tumor DNA to monitor metastatic breast cancer. N Engl J Med, Mar. 28, 2013; 368(13):1199-1209.
Docherty, S. J., et al. Bisulfite-based epityping on pooled genomic DNA provides an accurate estimate of average group DNA methylation. Epigenetics Chromatin, Mar. 10, 2009; 2(1):3.
Kaplow, I. M., et al. A pooling-based approach to mapping genetic variants associated with DNA methylation. Genome Res 2015; 25(6):907-917.
Byun, H. M., et al. Temporal stability of epigenetic markers: sequence characteristics and predictors of short-term DNA methylation variations. PLoS One, Jun. 2012; 7(6):e39220.

\* cited by examiner

% Methylation per base

% Methylation per base

PREDICTING THE OCCURRENCE OF METASTATIC CANCER USING EPIGENOMIC BIOMARKERS AND NON-INVASIVE METHODOLOGIES

CROSS-REFERENCE TO RELATED APPLICATIONS

The present application is the U.S. National Stage Entry of PCT/US16/27087, filed Apr. 12, 2016, which claims the benefit of U.S. Provisional Application Nos. 62/146,516 filed Apr. 13, 2015 and 62/216,477, filed Sep. 10, 2015, the contents of both of which are incorporated herein by reference for any purpose.

TECHNICAL FIELD

This application relates to the field of cell free nucleic acid-based cancer diagnostics and therapeutic agents and specifically to methods of diagnosing metastatic potential of one or more cancers, such as breast cancer.

BACKGROUND

Despite improvements in breast cancer screening, diagnosis, and treatment, there are patients who develop metastasis and succumb to their disease. Once patients develop metastatic breast cancer (MBC), their disease is treatable but not curable, and the 5-year survival for patients with MBC remains below 25%. The ability to predict which patients will develop distant disease recurrence is still based on relatively crude factors. A number of clinico-pathological criteria have been established as breast cancer prognostic markers and used to determine risk of recurrence and stratify patients into high and low risk groups. The risk of distant metastasis increases with bigger tumor size, the presence and number of lymph-node involvement (≥4 nodes have a higher recurrence risk), lack of estrogen receptor (ER) expression, over-expression of Her2, a high proliferative index, lymphovascular invasion, and loss of histopathological differentiation (grade). Even with these clinico-pathologic criteria, we are still unable to concretely define which groups of patients will be cured or will develop MBC regardless of whether they are stratified as having high-risk or low-risk disease.

Molecular profiles have improved our ability to determine the need of chemotherapy for those individuals who are at high-risk for recurrence. The most widely used multigene classifiers include the 21-gene Oncotype Dx signature (Genomic Health, USA), the 70-gene MammaPrint signature (Agendia, Netherlands), the 76-gene Rotterdam signature and the PAM50 intrinsic classifier (NanoString, USA). Despite the huge quantity of information gleaned from these gene signatures, none can precisely predict the clinical course of an individual and rely on the presence of tissue at a single time point. Therefore, they are not able to monitor risk of recurrence after completion of therapy due to residual disease. Not unlike the clinicopathologic features, there are patients deemed high-risk who do very well with standard therapy and never experience a recurrence and patients with low-risk profiles who still die of breast cancer. There also remains a risk of recurrence even after the most effective chemotherapy agents are administered to high-risk patients. Another strategy for stratifying patients as high-risk for systemic recurrence is pathologic status after neoadjuvant systemic therapy. The presence of a complete pathologic response by clinical metrics to pre-operative systemic therapy has been shown to correlate with overall survival. However, recent meta-analyses have not demonstrated a correlation with complete response with disease free survival or overall survival.

Cancer metastases arise from disseminated cells of the primary tumor mass before treatment and/or from minimal residual disease (MRD) persisting after therapy (collectively known as micrometastatic disease). Patients with cancer present with different disease statuses as it relates to the degree of metastatic spread. Cancer cells spread throughout the body in a process referred to as 'The Metastatic Cascade'. The process begins when malignant cells from the primary tumor acquire invasive phenotypes, penetrate the extracellular matrix, and pass into the bloodstream. Circulating tumor cells (CTC) then travel through the bloodstream until they become trapped, usually in capillaries downstream of the point of entry. Here the cells adhere to the basement membrane and make a metastatic deposit. The new cells undergo angiogenesis and begin to grow as a macrometastasis in their new site. There is a phase during the metastatic process where detection of micrometastatic cells may lead to prevention of macrometastatic lesions, which are incurable.

Currently there are still no effective methods to determine which patients harbor micrometastatic disease after standard breast cancer therapy and who will eventually develop local or distant recurrence. It would be advantageous to determine the subset of patients who harbor micrometastatic cells and develop trials, which would evaluate the use of additional therapy for eventual prevention of metastasis. There is a need to identify epigenomic biomarkers in metastatic cancer to accurately and repeatedly predict the likelihood of metastases. These biomarkers would allow for earlier diagnosis of metastases and the development of new therapeutic targets to control this fatal manifestation of cancer.

SUMMARY

The present technology provides a method of determining whether a subject with cancer is likely to experience one or more metastases. The method may include determining a methylation level of at least one gene selected from the group consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2 in a subject-derived sample and then comparing the subject-derived methylation level with a normal control level obtained from a normal sample. Thereafter, the method may include determining that the subject with cancer is likely to experience one or more metastases when an increase of said subject-derived methylation level as compared to the normal control level in the step described above.

In certain aspects, the methylation levels of genes in subject-derived brain or breast tissue are determined with bisulfite treatment of DNA, reverse phase high pressure liquid chromatography (HPLC), methylation sensitive PCR (MSP), whole genome bisulfite sequencing (WGBS), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, methylation detection after restriction, methylation-sensitive restriction fingerprinting, restriction landmark genomic scanning (RLGS), or bisulfite conversion combined with bisulfite restriction analysis (COBRA).

Some embodiments may provide a method for determining whether a subject with cancer is likely to experience one or more metastases. For example, the method may include obtaining a cell-free sample from the subject; extracting nucleic acids (e.g., DNA) from the cell-free sample; using the nucleic acids extracted from the cell-free sample, determining a methylation level of at least one gene (e.g., 10 or more) selected from the group consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2; comparing the subject-derived methylation level with a normal control level obtained from a normal sample; and/or determining that the subject with cancer is likely to experience one or more metastases when an increase of said subject-derived methylation level as compared to the normal control level is detected in the step described above. In some aspects, the methylation levels of the genes in the extracted nucleic acids may be determined using bisulfite treatment of DNA, whole genome bisulfite sequencing (WGBS), reverse phase high pressure liquid chromatography (HPLC), methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, methylation detection after restriction, methylation-sensitive restriction fingerprinting, restriction landmark genomic scanning (RLGS), or bisulfite conversion combined with bisulfite restriction analysis (COBRA). In some aspects, the cell-free sample may comprise plasma or serum.

Some additional embodiments may provide a method for determining whether a subject with cancer is likely to experience one or more metastases. For example, the method may include obtaining a non-invasive sample from the subject; extracting DNA from the non-invasive sample; using the DNA extracted from the non-invasive sample, determining a methylation level of each of the following genes: BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, VWC2; comparing the subject-derived methylation level with a normal control level obtained from a normal sample; and determining that the subject with cancer is likely to experience one or more metastases when an increase of said subject-derived methylation level as compared to the normal control level is detected in the step described above. In some aspects, the non-invasive sample is at least one of whole blood, plasma, and serum and the method may further comprise administering one or more prophylactic therapies to the subject if the subject is diagnosed as likely to experience one or more metastases.

DETAILED DESCRIPTION

Figure 1:
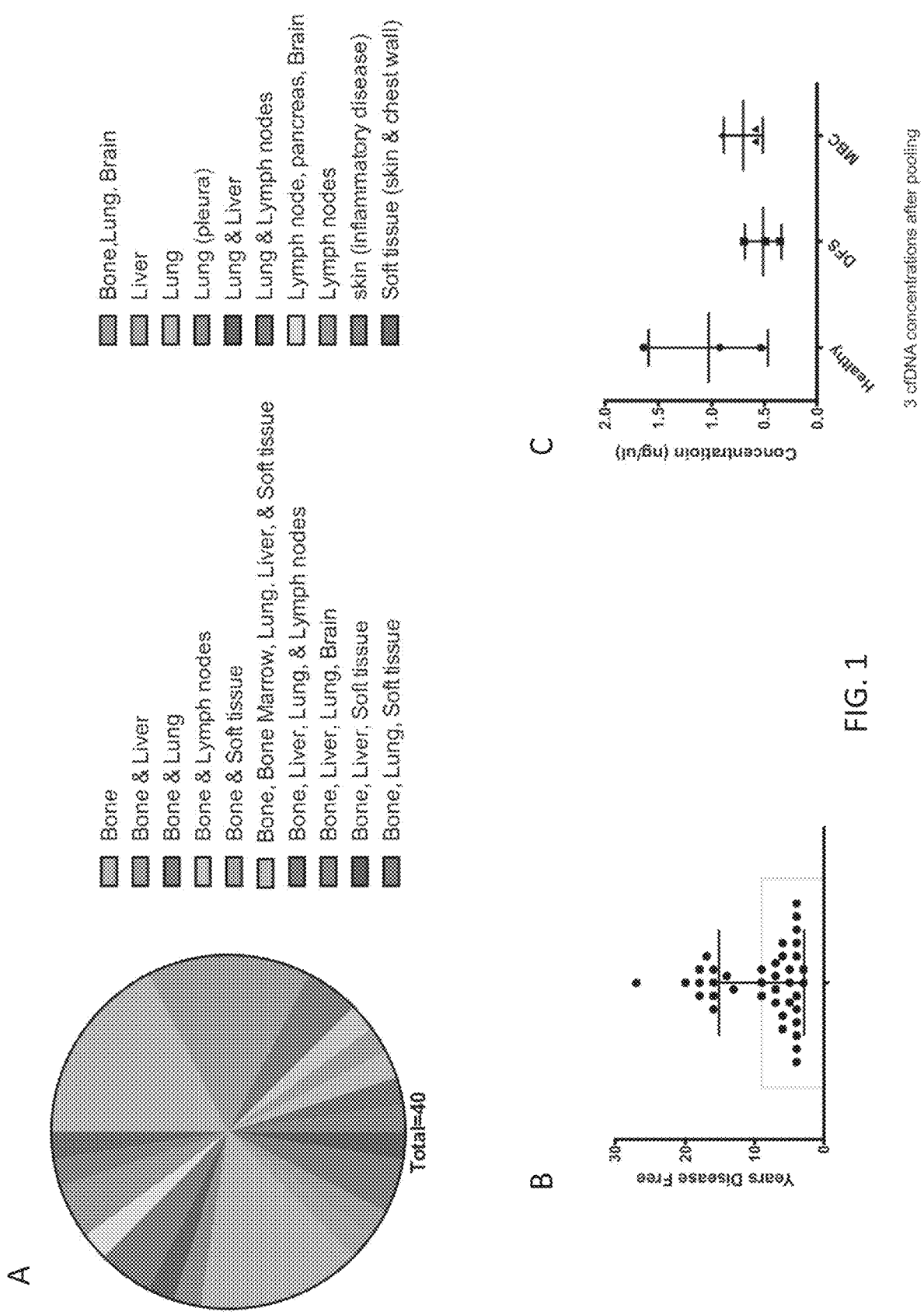
FIGS. 1A-1C depicts an analysis of 120 clinically annotated plasma samples for the Komen Tissue Bank representing 40 samples from Healthy individuals, 40 from disease free survivors (DFS) and 40 from patients with metastatic breast cancer (MBC). A) Pie chart shows distribution of involved sites of distant metastases in the MBC group. B) Vertical plot shows the number of years disease free in the DFS group. Two clusters are evident. C) Plot shows cfDNA concentrations from three independent extractions obtained after samples were pooled into three groups.

The present technology is directed to methods of diagnosing and treating metastatic cancer (e.g., breast cancer). In certain aspects, the diagnostic methods comprise an analysis the methylation state of at least one gene or one or more loci within one or more genes, which may be provided by one or more molecular techniques, such as methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, whole genome bisulfite sequencing (WGBS) methylation detection after restriction, methylation-sensitive restriction fingerprinting, restriction landmark genomic scanning (RLGS), or bisulfite conversion combined with bisulfite restriction analysis (COBRA). The investigators believe there is a predictive clinical window of opportunity to detect microscopic disease in the pre-macrometastatic setting before micrometastases lead to incurable macrometastases years after initial diagnosis.

Human blood is easily accessible for sampling and contains informational cues from tumors, which "leak" protein and DNA into circulation. In the last few years, circulating cell-free (cf)DNA has attracted attention for clinical use in the context of risk prediction, prognostication and prediction of response to chemotherapy in human cancer. Early reports suggesting that the simple presence or absence of cfDNA itself, or its concentration was diagnostic, have been scrutinized, since high levels of cfDNA are not specific to neoplastic lesions and are also observed in several other pathologies, including pro-inflammatory and neurological disorders. In addition, cfDNA has also been found in healthy individuals in the same concentration range of some cancer patients. Data has corroborated this finding by demonstrating a fairly equal distribution of DNA in plasma from healthy individuals, disease free survivors (DFS) and MBC patients. This argues that the presence of tumor-specific alterations is the best criterion to assess the tumoral origin of cfDNA. Various types of DNA alterations have been reported in cfDNA including, point mutations, microsatellite instabilities, loss of heterozygosity and DNA hypermethylation. DNA methylation is a centrally important modification for the maintenance of large genomes. The essentiality of proper DNA methylation maintenance is highlighted in cancer, where normal patterns are lost. Aberrant DNA methylation is among the earliest and most chemically stable molecular alterations in cancer, making it a potentially useful biomarker for early detection or risk prediction. The high degree of detection sensitivity of aberrantly methylated loci is afforded by the frequency of the occurrence (for example, compared to somatic mutations) and because bisulfite modification provides detection of hypermethylated targets in large excess of unmethylated ones (1:1000). Several groups have now reported the detection of tumor-associated methylation changes in cfDNA extracted from plasma or serum but none have been studied or proven for the prediction of metastasis in the early stage setting.

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions ($Mg^{2+}$); and monovalent cation potassium ions.

PCR technology relies on thermal strand separation followed by thermal dissociation. During this process, at least one primer per strand, cycling equipment, high reaction temperatures and specific thermostable enzymes are used (U.S. Pat. Nos. 4,683,195 and 4,883,202). Alternatively, it is possible to amplify the DNA at a constant temperature (Nucleic Acids Sequence Based Amplification (NASBA) Kievits, T., et al., J. Virol Methods, 1991; 35, 273-286; and Malek, L. T., U.S. Pat. No. 5,130,238; T7 RNA polymerase-mediated amplification (TMA) (Giachetti C, et al. J Clin Microbiol 2002 July; 40(7):2408-19; or Strand Displacement Amplification (SDA), Walker, G. T. and Schram, J. L., European Patent Application Publication No. 0 500 224 A2; Walker, G. T., et al., Nuc. Acids Res., 1992; 20, 1691-1696).

Thermal cycling subjects the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step—94-96° C.; denaturation step—94-98° C.; annealing step—50-65° C.; extension/elongation step—70-74° C.; final elongation-70-74° C.; final hold-4-10° C.

Real-time polymerase chain reaction, also called quantitative real time polymerase chain reaction (QRT-PCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

Amplified nucleic acid can be detected using a variety of detection technologies well known in the art. For example, amplification products may be detected using agarose gel by performing electrophoresis with visualization by ethidium bromide staining and exposure to ultraviolet (UV) light, by sequence analysis of the amplification product for confirmation, or hybridization with an oligonucleotide probe.

The oligonucleotide probe may comprise a flourophore and/or a quencher. The oligonucleotide probe may also contain a detectable label including any molecule or moiety having a property or characteristic that is capable of detection, such as, for example, radioisotopes, fluorophores, chemiluminophores, enzymes, colloidal particles, and fluorescent microparticles.

Probe sequences can be employed using a variety of methodologies to detect amplification products. Generally all such methods employ a step where the probe hybridizes to a strand of an amplification product to form an amplification product/probe hybrid. The hybrid can then be detected using labels on the primer, probe or both the primer and probe. Examples of homogeneous detection platforms for detecting amplification products include the use of FRET (fluorescence resonance energy transfer) labels attached to probes that emit a signal in the presence of the target sequence. "TaqMan" assays described in U.S. Pat. Nos. 5,210,015; 5,804,375; 5,487,792 and 6,214,979 (each of which is herein incorporated by reference) and Molecular Beacon assays described in U.S. Pat. No. 5,925,517 (herein incorporated by reference) are examples of techniques that can be employed to detect nucleic acid sequences. With the "TaqMan" assay format, products of the amplification reaction can be detected as they are formed or in a so-called "real time" manner. As a result, amplification product/probe hybrids are formed and detected while the reaction mixture is under amplification conditions.

For example, the PCR probes may be TaqMan™ probes that are labeled at the 5' end with a fluorophore and at the 3'-end with a quencher molecule. Suitable fluorophores and quenchers for use with TaqMan® probes are disclosed in U.S. Pat. Nos. 5,210,015, 5,804,375, 5,487,792 and 6,214, 979 and WO 01/86001 (Biosearch Technologies). Quenchers may be Black Hole Quenchers disclosed in WO 01/86001.

Nucleic acid hybridization can be done using techniques and conditions known in the art. Specific hybridization conditions will depend on the type of assay in which hybridization is used. Hybridization techniques and conditions can be found, for example, in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York) and Sambrook et al. (1989) Molecular Cloning. A Laboratory Manual (2d ed., Cold Spring Harbor Laboratory Press, Plainview, N.Y.).

Hybridization of nucleic acid may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified. Alternatively, stringency conditions can be adjusted to allow some mismatching in sequences so that lower degrees of similarity are detected.

It is understood in the art that a nucleic acid molecule need not be 100% complementary to a target nucleic acid sequence to be specifically hybridizable. That is, two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30 degrees C. for short probes (e.g., 10 to 50 nucleotides) and at least about 60 degrees C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37 degrees C., and a wash in 1.times. to 2 times.SSC (20.times.SSC=3.0 M NaCl/0.3 M trisodium citrate) at 50 to 55.degree. C. Exemplary moderate stringency conditions include hybridization in 40 to 45% formamide, 1.0 M NaCl, 1% SDS at 37 degrees C., and a wash in 0.5.times. to 1.times SSC at 55 to 60.degree. C. Exemplary high stringency conditions include hybridization in 50% formamide, 1 M NaCl, 1% SDS at 37 degrees C., and a wash in 0.1.times.SSC at 60 to 65 degrees C. The duration of hybridization is generally less than about 24 hours, usually about 4 to about 12 hours, or less depending on the assay format.

It should be noted that the oligonucleotides of this disclosure can be used as primers or probes, depending on the intended use or assay format. For example, an oligonucleotide used as a primer in one assay can be used as a probe in another assay. The grouping of the oligonucleotides into primer pairs and primer/probe sets reflects certain implementations only. However, the use of other primer pairs comprised of forward and reverse primers selected from different preferred primer pairs is specifically contemplated.

There are several commercially available nucleic acid detection chemistries currently used in qPCR. These chemistries include DNA binding agents, FRET based nucleic acid detection, hybridization probes, molecular beacons, hydrolysis probes, and dye-primer based systems.

Methods of Determining DNA Methylation Levels

In the method of the technology, determining that gene expression is absent or low relative to a control may be considered to be evidence that the gene is methylated such that transcription of the gene (and thus translation of the protein) is inhibited. It will be recognized by those skilled in the art that a determination of gene expression that is absent or low relative to a control can be related to methylation status of the gene if desired by more direct analysis of the methylation status of the gene using any suitable method. Some non-limiting examples of suitable methods for analyzing DNA methylation include bisulfite treatment of DNA, reverse phase high pressure liquid chromatography (HPLC), methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, methylation detection after restriction, whole genome bisulfite sequencine (WGBS), methylation-sensitive restriction fingerprinting, restriction landmark genomic scanning (RLGS), and bisulfite conversion combined with bisulfite restriction analysis (COBRA).

In one embodiment, bisulfite treatment is used. The bisulfate method is used to convert unmethylated cytosines to uracil. The bisulfite treated DNA may be amplified and sequenced to determine the methylation status of CpG sites, where uracil is read as thymine (T) in the sequence of the amplified DNA when methylation is not present. However, since methylated cytosines are not converted to uracil by bisulfite treatment, they are read as cytosine (C), when analyzing methylated DNA.

In some embodiments, the method may include identifying increased methylation levels of at least one gene selected from the group consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least two genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least three genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least four genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least five genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least six genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least seven genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least eight genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least nine genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least ten genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least eleven genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least twelve genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least thirteen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least fourteen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least fifteen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least sixteen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least seventeen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least eighteen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least nineteen genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of at least twenty genes selected from the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In some aspects, the method may include looking at the methylation levels of all twenty-one of the genes on the list consisting of BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. For example, the method may include an assessment of some or all of these markers to make determinations regarding the likelihood of a cancer to metastasize from a primary tumor to other areas of a subject's body (e.g., the central nervous system).

In some embodiments of the technology, the twenty-one genes provided above may be located in anyone of a variety of physical locations (i.e., chromosomes and CpG islands) throughout the genome of a subject. For example, the physical locations of the twenty-one gene can be as follows in Table 1.

TABLE 1

Genomic Coordinates and CpG Island Numbers of Methylation Panel Members

| Gene Name | Genomic Coordinates | CpG Island Number |
|---|---|---|
| BEND4 | chr4: 42,153,075-42,154,982 | 201 |
| C1QL3 | chr10: 16,561,999-16,564,031 | 188 |
| CD01 | chr5: 115,152,294-115,152,688 | 122 |
| CDH4 | chr20: 59,826,973-59,828,970 | 230 |
| ERG | chr21: 40,032,252-40,033,659 | 140 |
| GP5 | chr3: 194,117,898-194,119,055 | 109 |
| GSC | chr14: 95,234,553-95,235,577 | 191 |
| HTR1B | chr6: 78,172,195-78,173,836 | 131 |
| LMX1B | chr9: 129,387,878-129,389,227 | 214 |
| MCF2L2 | chr3: 182,896,543-182,897,377 | 49 |
| PCDH10 | chr4: 134,069,171-134,073,941 | 162 |
| PENK | chr8: 57,358,236-57,358,832 | 138 |
| REC8 | chr14: 24,640,732-24,642,022 | 79 |
| RUNX3 | chr1: 25,255,582-25,257,088 | 311 |
| SP8 | chr7: 20,823,615-20,825,273 | 196 |
| SP9 | chr2: 175,199,496-175,202,622 | 295 |
| STAC2 | chr17: 37,381,334-37,381,637 | 150 |
| ULBP1 | chr6: 150,284,675-150,286,513 | 196 |
| UNC13A | chr19: 17,716,724-17,717,185 | 93 |
| VIM | chr10: 17,270,423-17,272,029 | 196 |
| VWC2 | chr7: 49,813,000-49,815,723 | 251 |

In some embodiments, the sample obtained from the subject with cancer that is analyzed for hypermethylation may be any variety of sample suitable for analysis. For example, the sample may comprise a whole blood/plasma/serum sample for methylation analysis using any of the methods described above or otherwise known in the art. In other words, in some aspects, the sample may comprise a non-invasive sample (e.g., a sample that can be obtained from the subject through simple/non-surgical methodologies, such as simple phlebotomy-based techniques). In other aspects, the sample may comprise a tissue sample from any portion of the subject (e.g., a primary tumor) that could be suitable for analysis.

Methods of Treating Breast Cancer CNS Metastasis

In certain aspects, the present technology provides methods of treatment of a metastatic tumor in a subject. The method of treatment may comprise administration of Vidaza, Entinostat, and/or PARP inhibitors to the subject. In some embodiments, the method may also include prophylactically treating the subject to in the event of a detection of some or all of the hypermethylation markers described above. For example, after an analysis of the methylation status of one or more of the markers described above reveals that the subject is likely to manifest one or more metastases from a primary tumor, the subject can receive one or more treatments to reduce and/or eliminate the potential for metastatic growth and/or reduce, retard, and/or eliminate any metastatic growth that has occurred to date in the subject. In some aspects, the treatment may include any pharmaceutical and/or other therapeutic interventions, such as, but not limited to chemotherapeutics, radiation, etc. that are now known or later developed.

Azacitidine (INN) or 5-azacytidine, sold under the trade name Vidaza, is a chemical analogue of cytidine, a nucleoside present in DNA and RNA. Azacitidine and its deoxy derivative, decitabine (also known as 5-aza-2'deoxycytidine), are used in the treatment of myelodysplastic syndrome. Both drugs were first synthesized in Czechoslovakia as potential chemotherapeutic agents for cancer. Vidaza can be used to remove methyl groups from DNA. This may weaken the effects of gene silencing mechanisms that occurred prior to the methylation. Methylation events are therefore believed to secure the DNA in a silenced state. Demethylation may reduce the stability of silencing signals and thus confer relative gene activation.

Entinostat, also known as SNDX-275 and MS-275, is a benzamide histone deacetylase inhibitor undergoing clinical trials for treatment of various cancers. Entinostat inhibits class I HDAC1 and HDAC3 with $IC_{50}$ of 0.51 μM and 1.7 μM, respectively.

PARP inhibitors are a group of pharmacological inhibitors of the enzyme poly ADP ribose polymerase (PARP). They are developed for multiple indications; the most important is the treatment of cancer. Several forms of cancer are more dependent on PARP than regular cells, making PARP an attractive target for cancer therapy. PARP1 is a protein that is important for repairing single-strand breaks ('nicks' in the DNA). If such nicks persist unrepaired until DNA is replicated (which must precede cell division), then the replication itself can cause double strand breaks to form. Drugs that inhibit PARP1 cause multiple double strand breaks to form in this way, and in tumours with BRCA1, BRCA2 or PALB2 mutations these double strand breaks cannot be efficiently repaired, leading to the death of the cells. Normal cells that do not replicate their DNA as often as cancer cells, and that lacks any mutated BRCA1 or BRCA2 still have homologous repair operating, which allows them to survive the inhibition of PARP.

In one embodiment, the method for treating cancer may include administering a pharmaceutical composition that includes a pharmaceutically acceptable carrier and a therapeutically effective amount of a substance that targets and inhibits the hypermethylated markers, including BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2. In other embodiments, the method may include a substance that targets any hypomethylated aspects of the subject's genome. In another embodiment, the pharmaceutical composition may also include a therapeutically effective amount of a substance that targets a receptor for the targeted biologic therapy.

DNA methylation inhibitors and methods for treating cancer with DNA methylation inhibitors, as well as for treating an individual with a DNA methylation inhibitor in combination with other agents, such as a histone deacetylase inhibitor, are known in the art. Some examples are provided in U.S. Pat. No. 7,276,228 and U.S. Patent Publication Nos. 20080175814 and 20070105792. The descriptions of methylation inhibitors, histone deacetylase inhibitors, and methods of using such agents for treating cancer in an individual are incorporated herein by reference. Identification of an individual as a candidate for receiving a DNA methylation inhibitor is also considered to be an indicative that the individual is a candidate for receiving a histone deacetylase inhibitor in combination with the DNA methylation inhibitor. In one embodiment, the histone deacetylase inhibitor may be Trichostatin A (TSA).

In certain aspects, the method for treating cancer comprises administering a DNA methylation inhibitor selected from the group consisting of 5-aza-2'-deoxycytidine (5-azadc), 5-azacytidine, and combinations thereof.

In one embodiment, an inhibitor may include any suitable substance able to target intracellular proteins, small molecules, or nucleic acid molecules alone or in combination with an appropriate carrier or vehicle, including, but not limited to, an antibody or functional fragment thereof, (e.g., Fab', F(ab')2, Fab, Fv, recombinant IgG, and scFv fragments and genetically engineered or otherwise modified forms of immunoglobulins such as intrabodies and chimeric antibodies), small molecule inhibitors of the protein, chimeric proteins or peptides, gene therapy for inhibition of transcription, or an RNA interference (RNAi)-related molecule or morpholino molecule able to inhibit gene expression and/or translation. In one embodiment the inhibitor is an RNAi-related molecule such as an siRNA or an shRNA for inhibition of translation. An RNA interference (RNAi) molecule is a small nucleic acid molecule, such as a short interfering RNA (siRNA), a double-stranded RNA (dsRNA), a micro-RNA (miRNA), or a short hairpin RNA (shRNA) molecule, that complementarily binds to a portion of a target gene or mRNA so as to provide for decreased levels of expression of the target.

The pharmaceutical compositions of the subject technology can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the technology. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. In one embodiment, the pharmaceutically acceptable carrier is a PEGylated immunoliposome for encapsulating the RNAi-related molecule. The PEGylated immunoliposomes or other carrier or delivery vehicle may be specifically targeted to breast cancer tumor cells by conjugating recombinant human and/or chimeric monoclonal antibodies or functional fragments thereof to the liposomal membrane which are specific for cell surface protein and/or carbohydrate and/or glycoprotein markers specific to the subtype that is targeted. Such markers that may be targeted include, but are not limited to, BEND4, CDH4, C1QL3, ERG, GP5, GSC, HTR1B, LMX1B, MCF2L2, PENK, REC8, RUNX3, PAX5, PCDH10, SP8, SP9, STAC2, ULBP1, UNC13A, VIM, and/or VWC2.

Compositions containing pharmaceutically acceptable carriers are described in a number of sources which are well known and readily available to those skilled in the art. For example, Remington: The Science and Practice of Pharmacy (Gerbino, P. P. [2005] Philadelphia, Pa., Lippincott Williams & Wilkins, 21st ed.) describes formulations that can be used in connection with the subject technology. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject technology can include other agents conventional in the art having regard to the type of formulation in question.

The pharmaceutical composition described above is administered and dosed in accordance with good medical practice, taking into account the clinical condition of the individual patient, the site and method of administration, scheduling of administration, patient age, sex, body weight, and other factors known to medical practitioners. The therapeutically effective amount for purposes herein is thus determined by such considerations as are known in the art. For example, an effective amount of the pharmaceutical composition is that amount necessary to provide a therapeutically effective decrease in the expression of the targeted gene. The amount of the pharmaceutical composition should be effective to achieve improvement including but not limited to total prevention and to improved survival rate or more rapid recovery, or improvement or elimination of symptoms associated with the chronic inflammatory conditions being treated and other indicators as are selected as appropriate measures by those skilled in the art. In accordance with the present technology, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of the patient and the route of administration.

The brain and other portions of the central nervous system are common sites of metastatic disease in patients with breast cancer and has few therapeutic options with dismal outcomes. A deep genomic profiling was performed, which integrated gene copy number, gene expression and DNA methylation datasets on a collection of breast brain metastases. Frequent large chromosomal gains in 1q, 5p, 8q, 11q, and 20q and frequent broad level deletions involving 8p, 17p, 21p and Xq were identified. Frequently amplified and overexpressed genes included ATAD2, BRAF, DERL1, DNMTRB and NEK2A. The ATM, CRYAB and HSPB2 genes were commonly deleted and underexpressed. Knowledge mining revealed enrichment in cell cycle and G2/M transition pathways, which contained AURKA, AURKB and FOXM1. Using the PAM50 breast cancer intrinsic classifier, Luminal B, Her2+/ER negative, and basal-like tumors were identified as the most commonly represented breast cancer subtypes in our brain metastasis cohort. While overall methylation levels were increased in breast cancer brain metastasis, basal-like brain metastases were associated with significantly lower levels of methylation. Integrating DNA methylation data with gene expression revealed defects in cell migration and adhesion due to hypermethylation and downregulation of PENK, EDN3, and ITGAM. Hypomethylation and upregulation of KRT8 likely affects adhesion and permeability. Genomic and epigenomic profiling of breast brain metastasis has provided insight into the somatic events underlying this disease, which have potential in forming the basis of future therapeutic strategies.

The following examples are given for purely illustrative and non-limiting purposes of the present technology.

Examples

In the examples contained herein, the investigators endeavored to employ circulating/cell-free (cf)DNA for clinical uses in the context of risk prediction, prognostication, and prediction of response to chemotherapy in human cancer. Discovery of new markers, as well as improvements in existing technologies, are needed to provide more robust, reproducible, quantitative, sensitive, and specific assays. Accordingly, the investigators characterized the plasma methylome of metastatic breast cancer (MBC) by paired-end whole-genome bisulfate sequencing (WGBS) to identify differentially methylated regions that were uniquely found in the circulation of MBC when compared with healthy (H) and disease-free survivors (DFS). MBC samples represented metastasis to usual sites including bone (n=23), liver (n=12), brain (n=3), lung (n=17), soft tissue (n=6) (FIG. 1A). All but 5 samples had involvement of more than one site. For the DFS cohort, the average years disease free was 9 years and the range was 3 years-27 years (FIG. 1B). Moreover, FIG. 1C illustrates the concentration of cfDNA of each of the pools of donors—healthy, DFS, and MBC.

Figure 2:
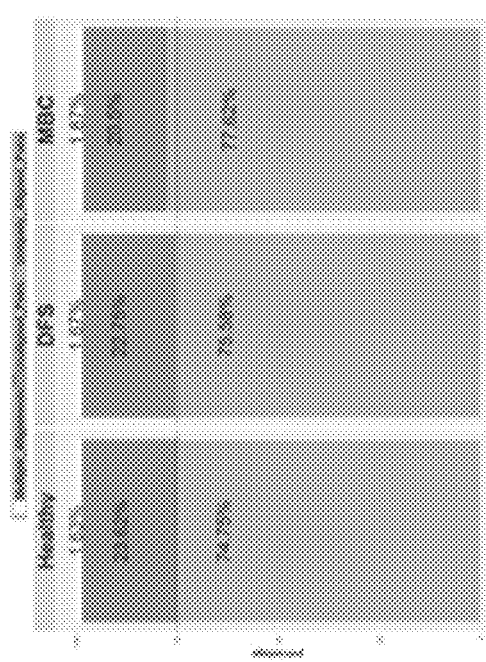
FIGS. 2A-2C depict library metrics for the examples reported herein. A) Gel image showing size distributions of template DNA for library preparation pre and post shearing. B) Bioanalyzer DNA100 electropherograms of libraries post preparation. C) Plot showing percent alignment rates for libraries.
Figure 2:
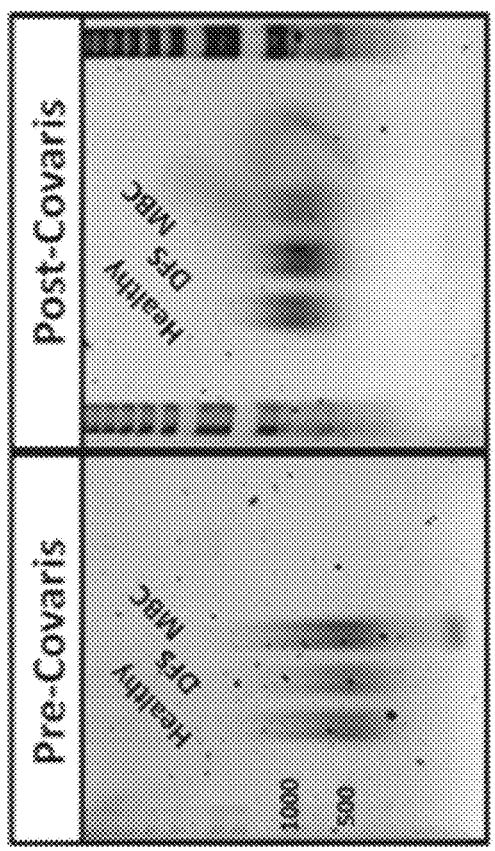
Figure 2:
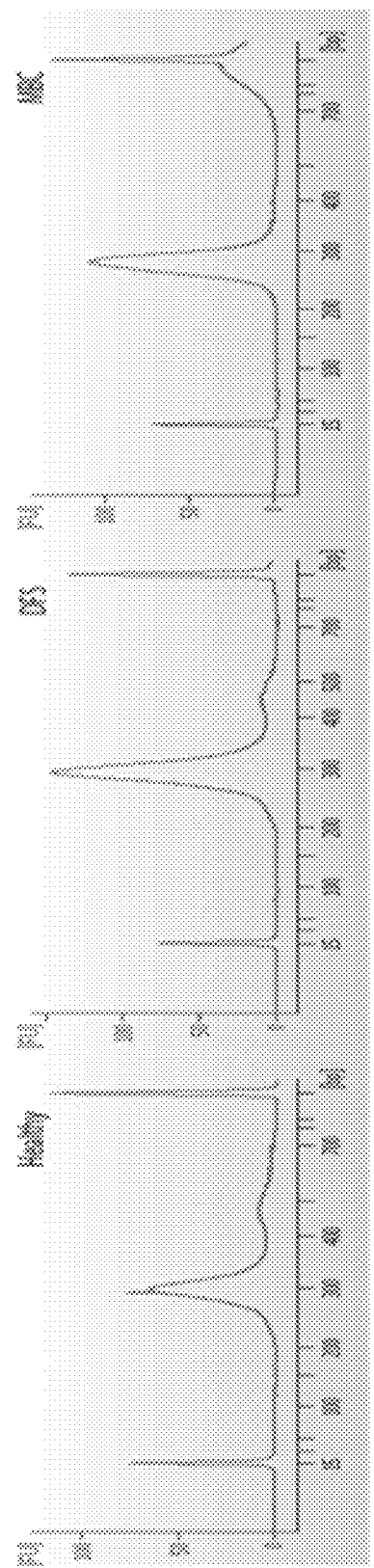

For quality control assurances, we confirmed that cfDNA fragment sizes were equal pre and post fragmentation; the DNA library yields and percent alignment rates were nearly equal for three sample pools (FIGS. 2A-2C). A total of approximately 504, 625, and 948 million reads were obtained for H, DFS, and MBC respectively, using 10 lanes of sequencing on an Illumina HiSeq 2500 (Table 2).

TABLE 2

|  | Healthy | DFS | MBC |
| --- | --- | --- | --- |
| Sequence pairs analysed in total | 504,714,070 | 624,589,963 | 948,134,127 |
| Number of paired-end alignments with a unique best hit | 377,297,268 | 472,055,818 | 735,966,733 |
| Mapping efficiency | 74.80% | 75.60% | 77.60% |
| Total number duplicated alignments removed | 150,624,996 | 177,334,052 | 217,843,901 |
| % of Total Number of Duplicated Alignments removed | 39.92 | 37.57 | 29.60 |
| Total count of deduplicated leftover sequences | 226,672,125 | 294,721,446 | 518,122,809 |
| Total count of deduplicated leftover sequences(%) | 60.08 | 62.43 | 70.40 |
| Total percentage of the original number of reads | 44.91 | 47.19 | 54.65 |
| Total number of methylation call strings processed | 453,344,250 | 589,442,892 | 1,036,245,618 |
| Total number of C's analysed | 7,415,876,103 | 9,530,584,696 | 15,514,763,236 |
| Total methylated C's in CpG context | 254,823,534 | 330,829,436 | 455,154,015 |
| Total C to T conversions in CpG context | 68,334,374 | 94,843,534 | 257,169,818 |
| C methylated in CpG context | 78.90% | 77.70% | 63.90% |
| read length | 101 | 101 | 101 |
| Genome Length | 3095693981 | 3095693981 | 3095693981 |
| Coverage after deduplication | 7.40 | 9.62 | 16.90 |
| Coverage after alignment and before deduplication | 12.31 | 15.40 | 24.01 |

Amongst these reads a mean of 64.3% of reads were nonduplicated. A final read count of ~227 (H), ~294 (DFS) and ~518 (MBC) million reads were used for downstream analyses. The average depth of coverage after deduplication was 7.4 (H), 9.62 (DFS) and 16.9 (MBC). The increased coverage in MBC was not due to global copy number alterations as shown by SVDetect.

Figure 3A:
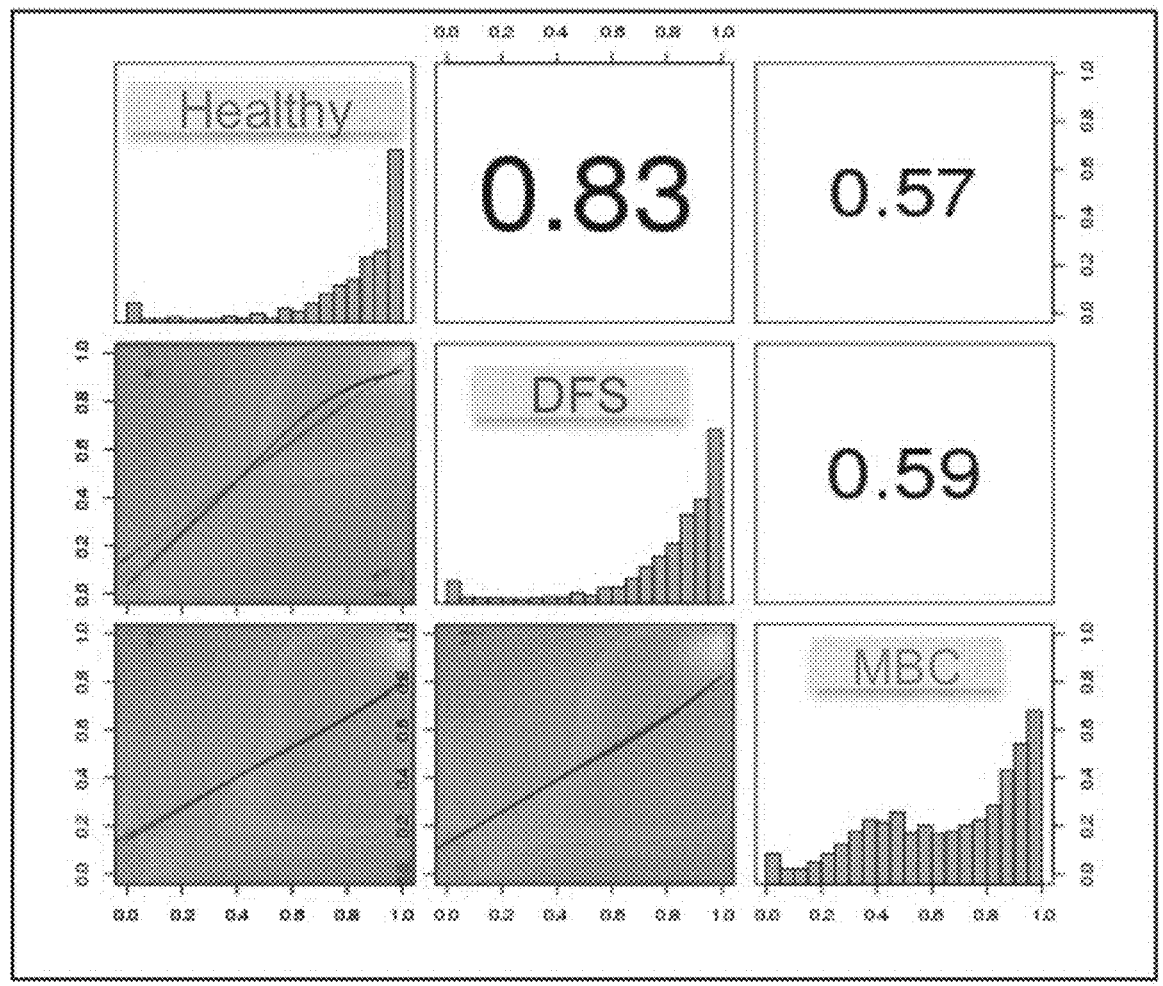
FIGS. 3A-3C illustrate that WGBS reveals MBC methylation profiles differs from DFS and H, which are similar. A) Heat scatterplots show % methylation values for pair-wise comparisons of three study groups. Numbers on upper right corner denote Pearson's correlation coefficients. The histograms on the diagonal are frequency of % methylation per cytosine for each pool. MBC demonstrates a shift to the left compared to the DFS and H, indicating genome-wide hypomethylation. B) Hierarchical clustering of methylation profiles for each pool using Pearson's correlation distance and Ward's clustering method. C) Principal Component Analysis (PCA) of the methylation profiles of each cfDNA pool, showing PC1 and PC2 for each sample. Samples closer to each other in clustering or principal component space are similar in their methylation profiles.
Figure 3B:
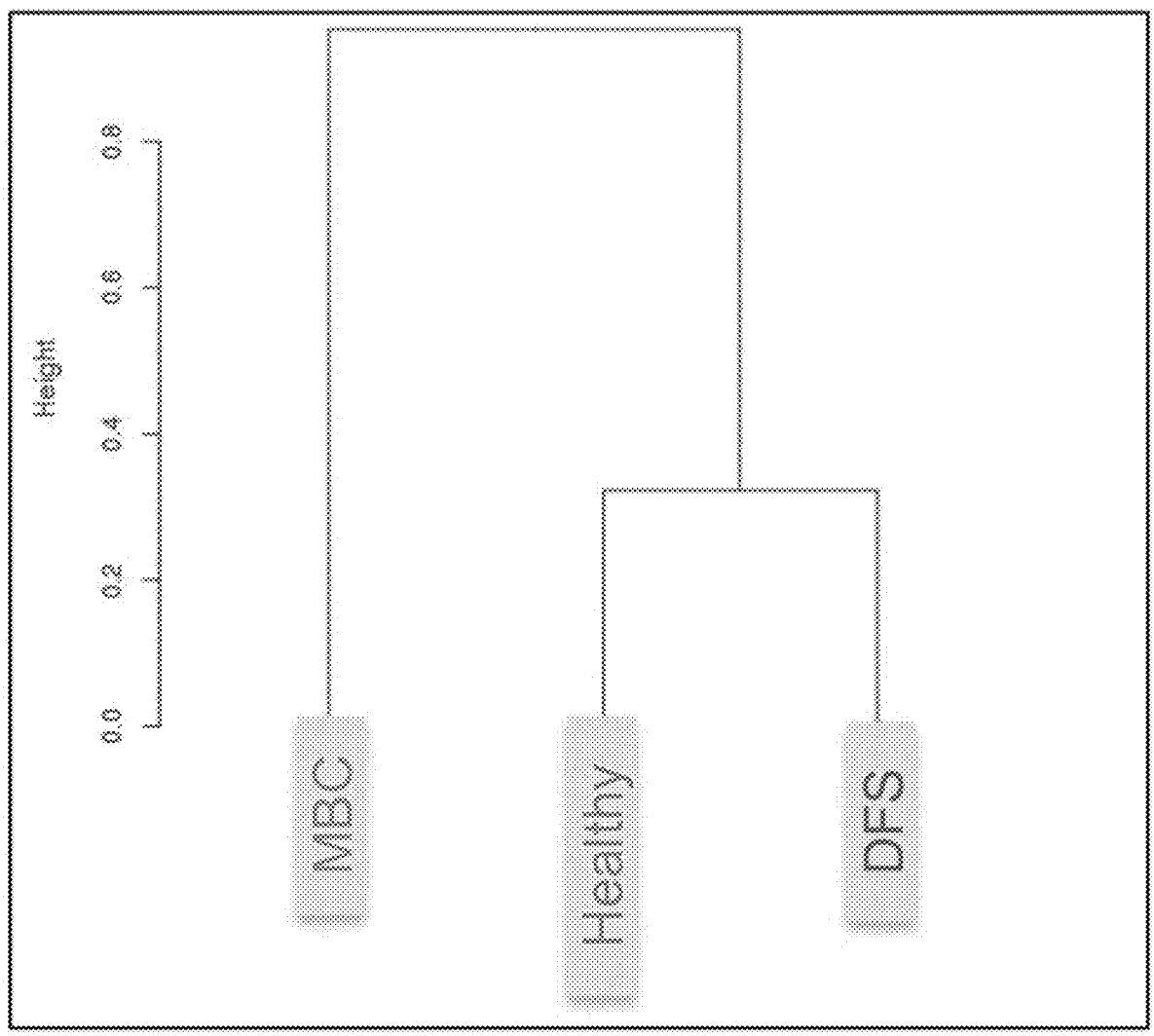
Figure 3C:
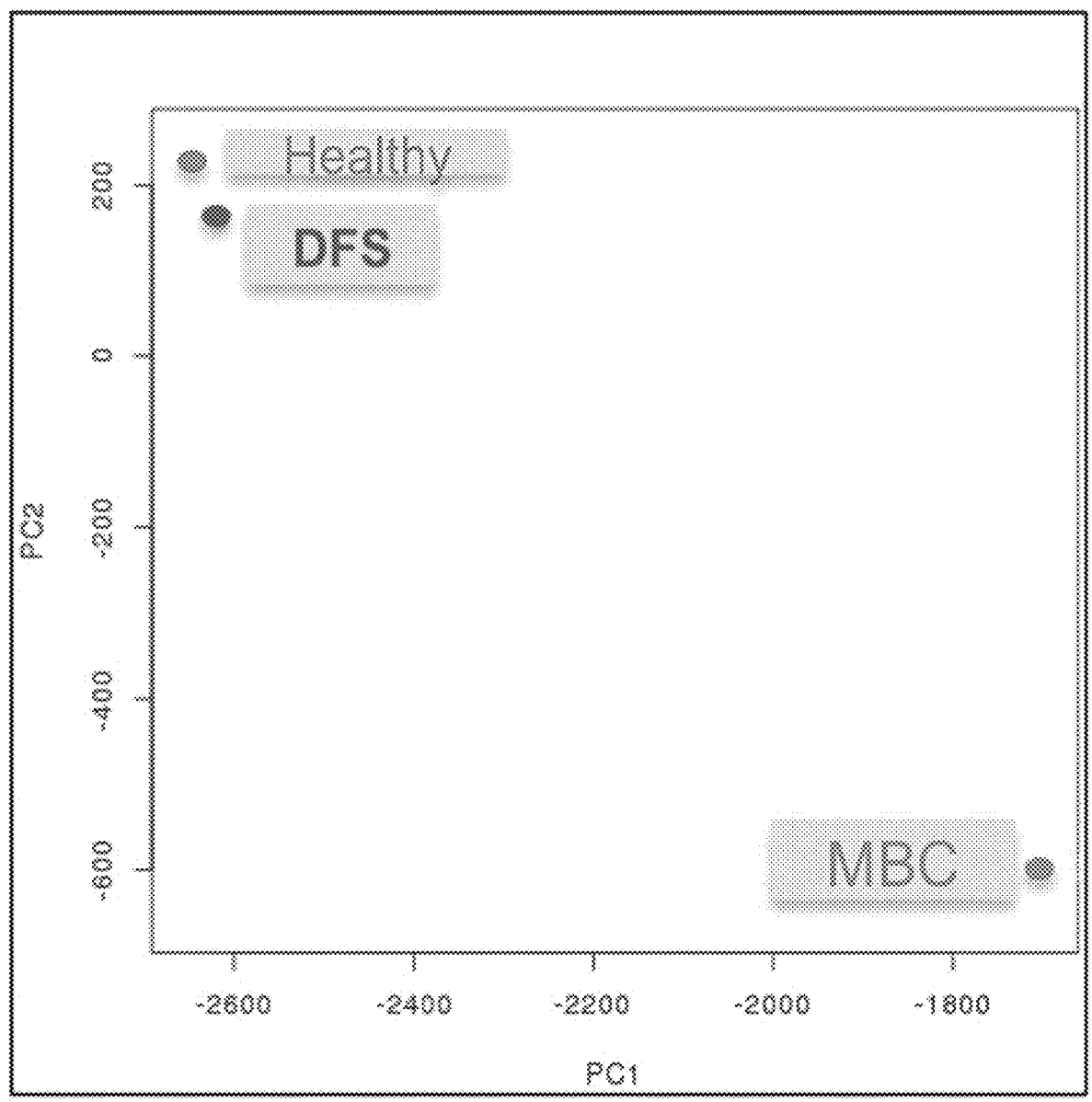
Figure 4:
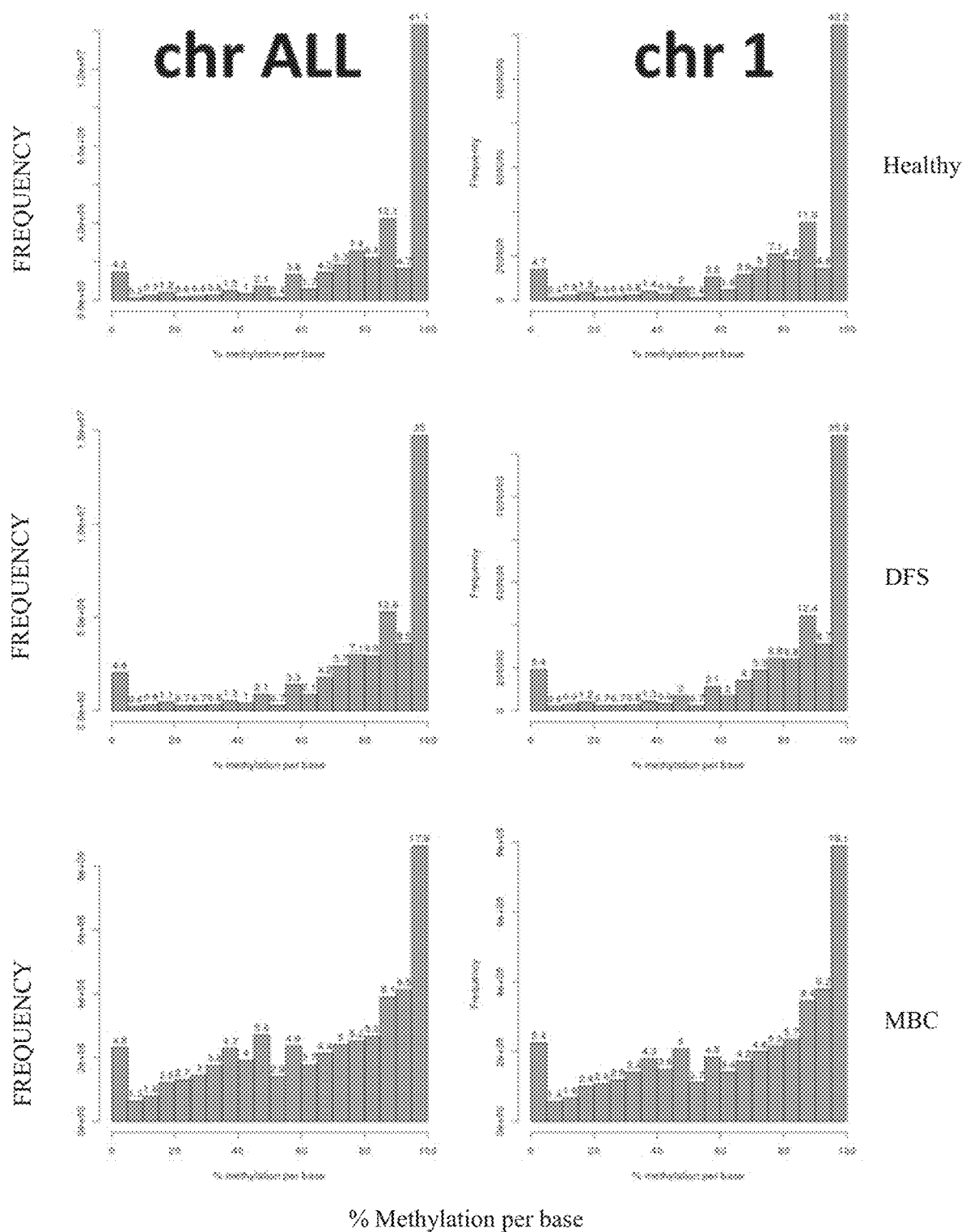
FIG. 4 depicts histogram plots of the frequency of % methylation per cytosine for each sample pool by chromosome. MBC demonstrates a shift to the left compared to the DFS and H in each chromosome.
Figure 4:
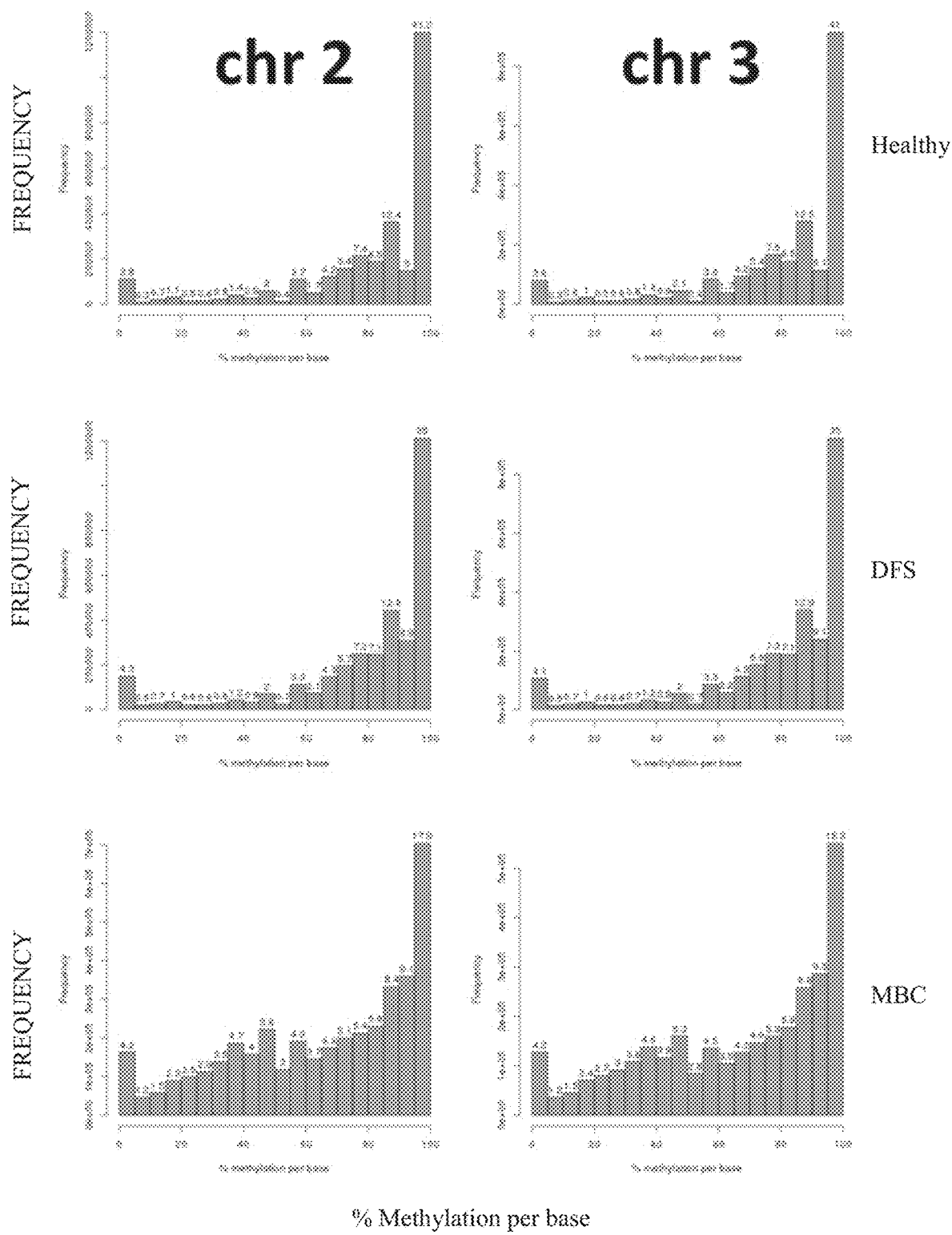
Figure 4:
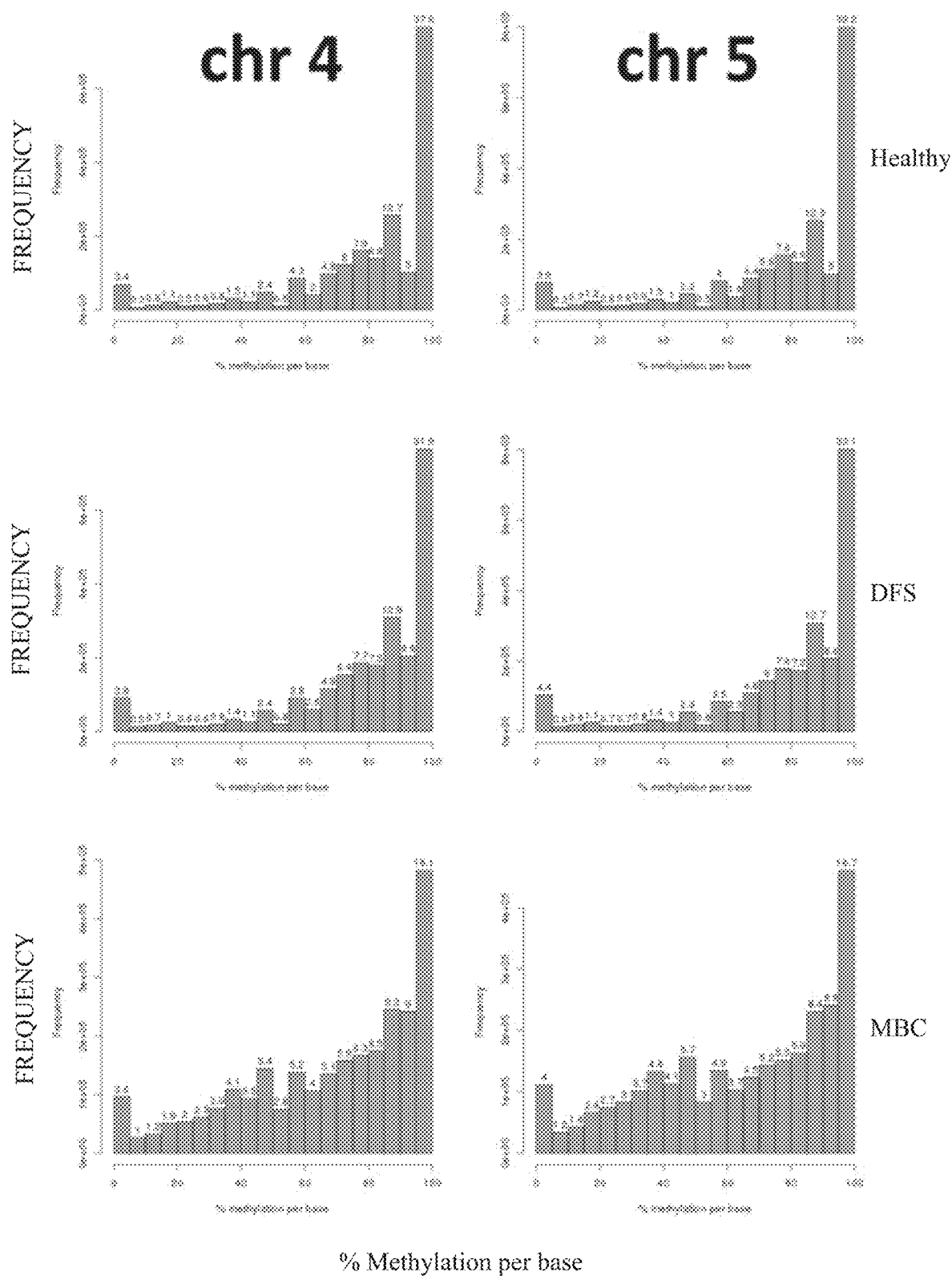
Figure 4:
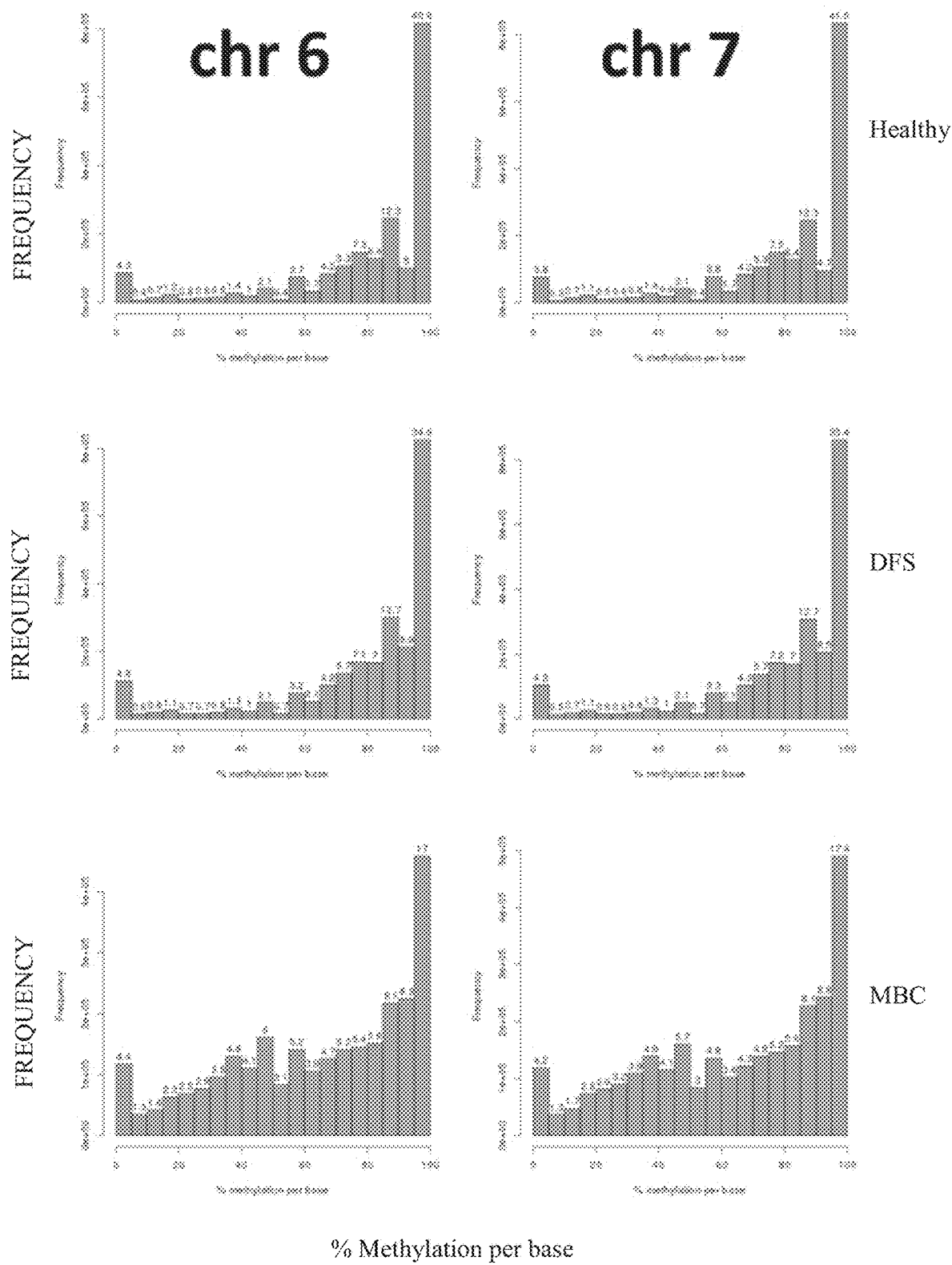
Figure 4:
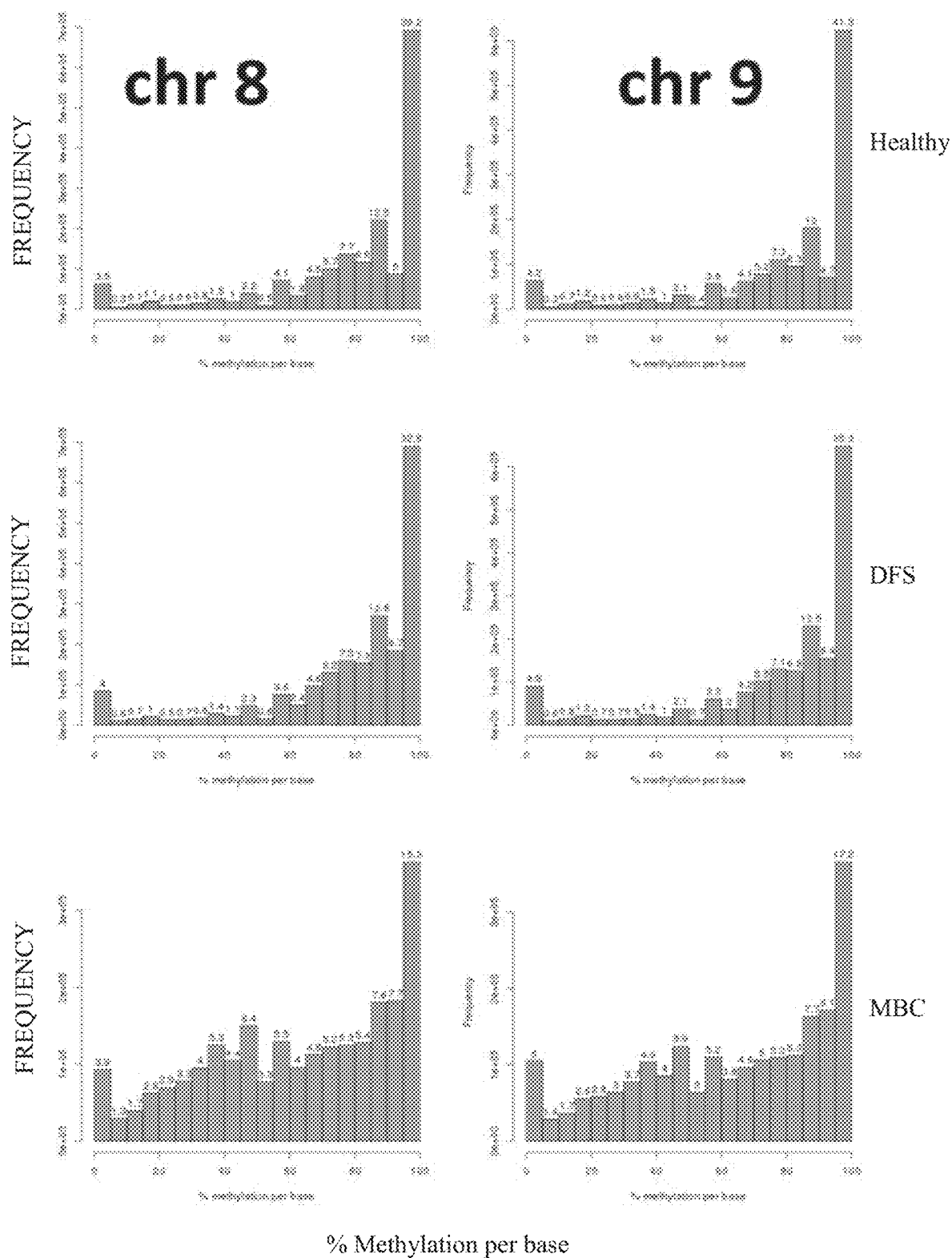
Figure 4:
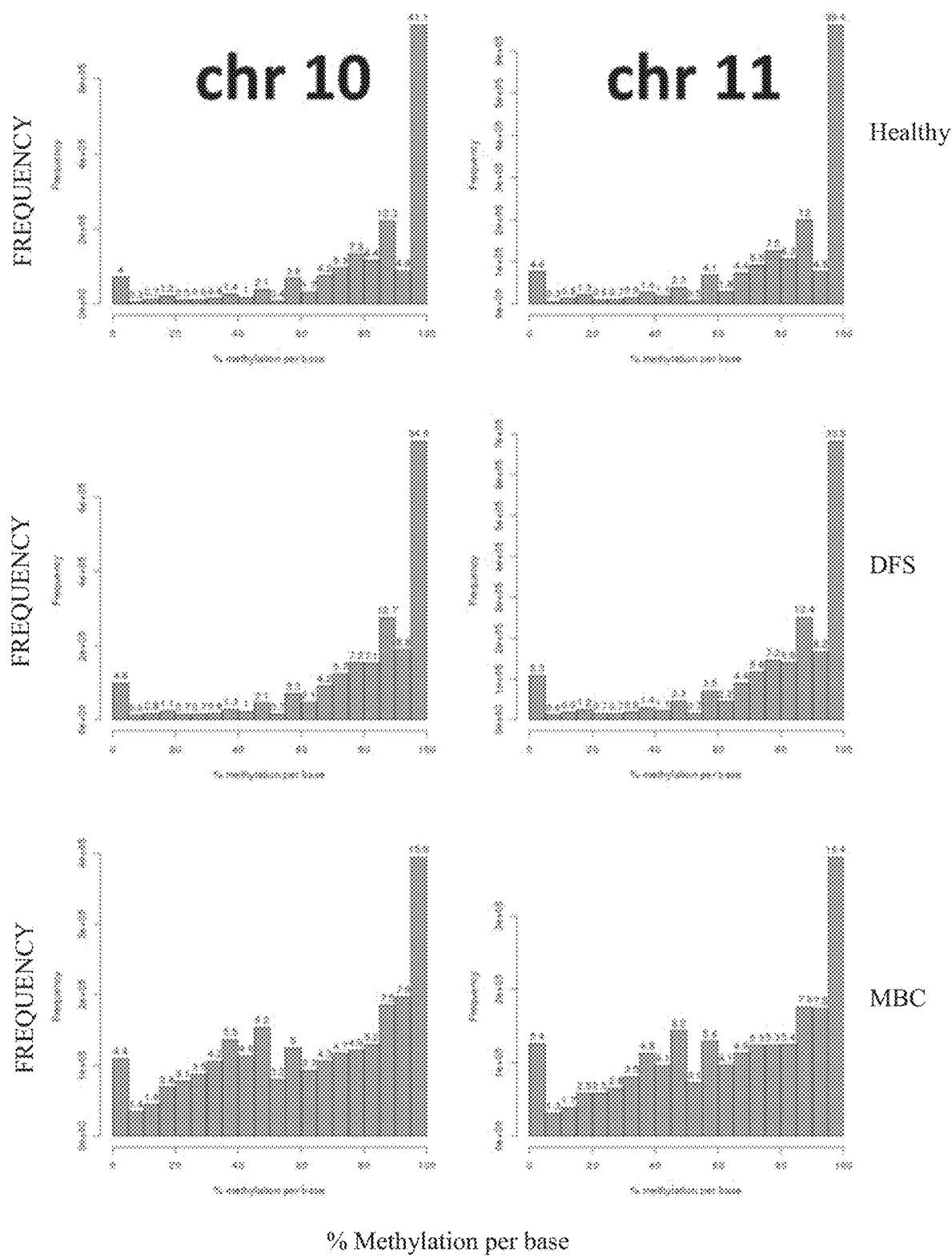
Figure 4:
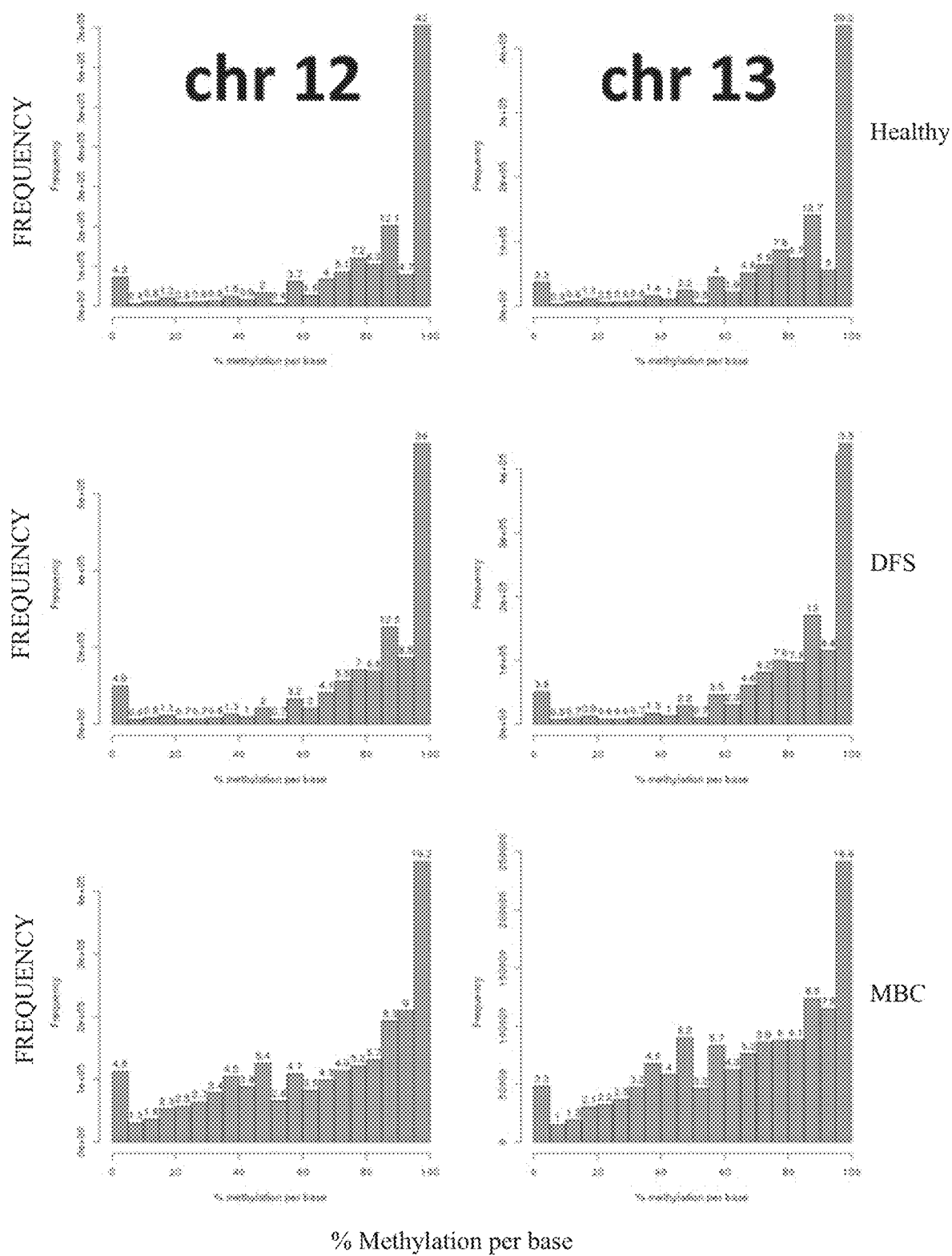
Figure 4:
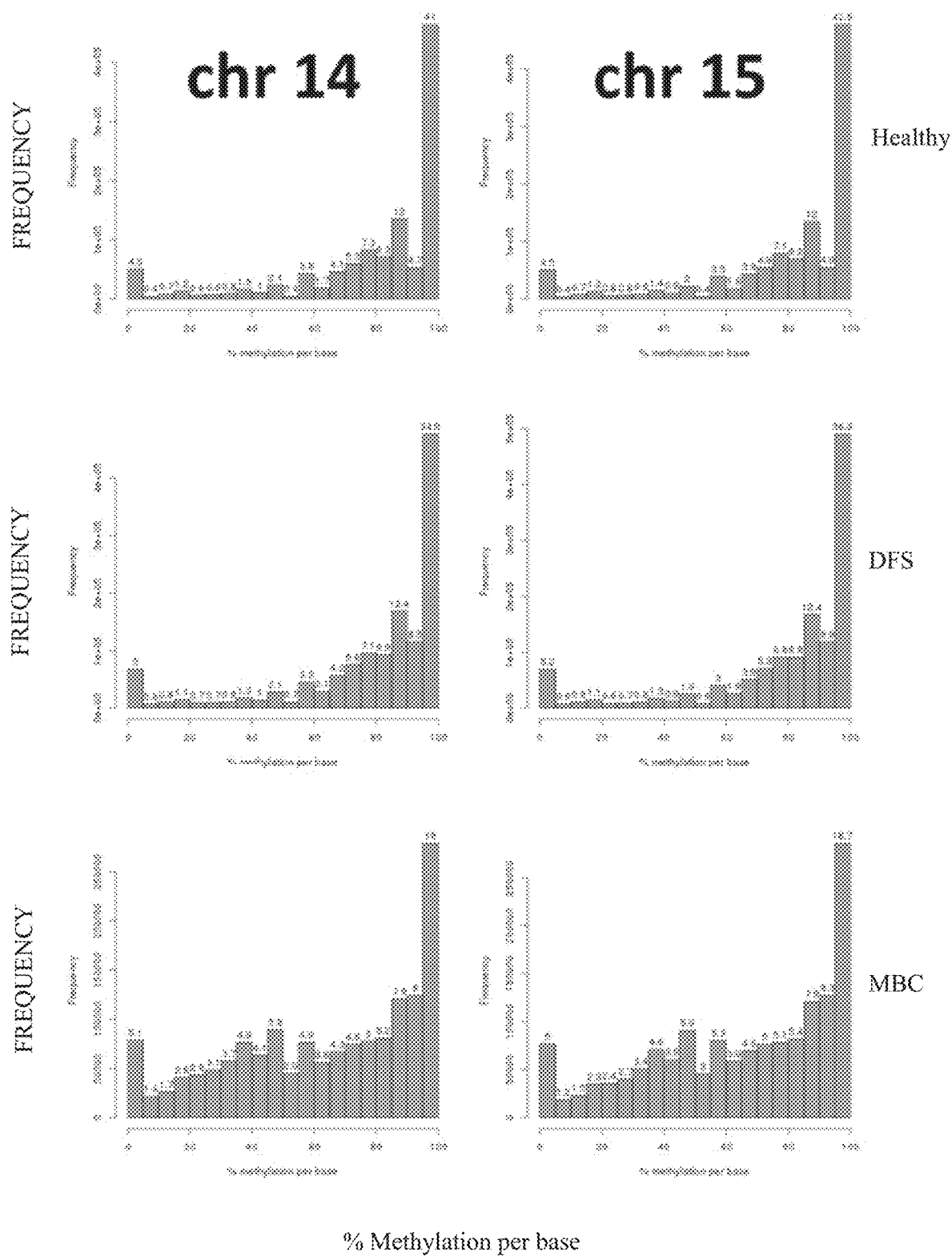
Figure 4:
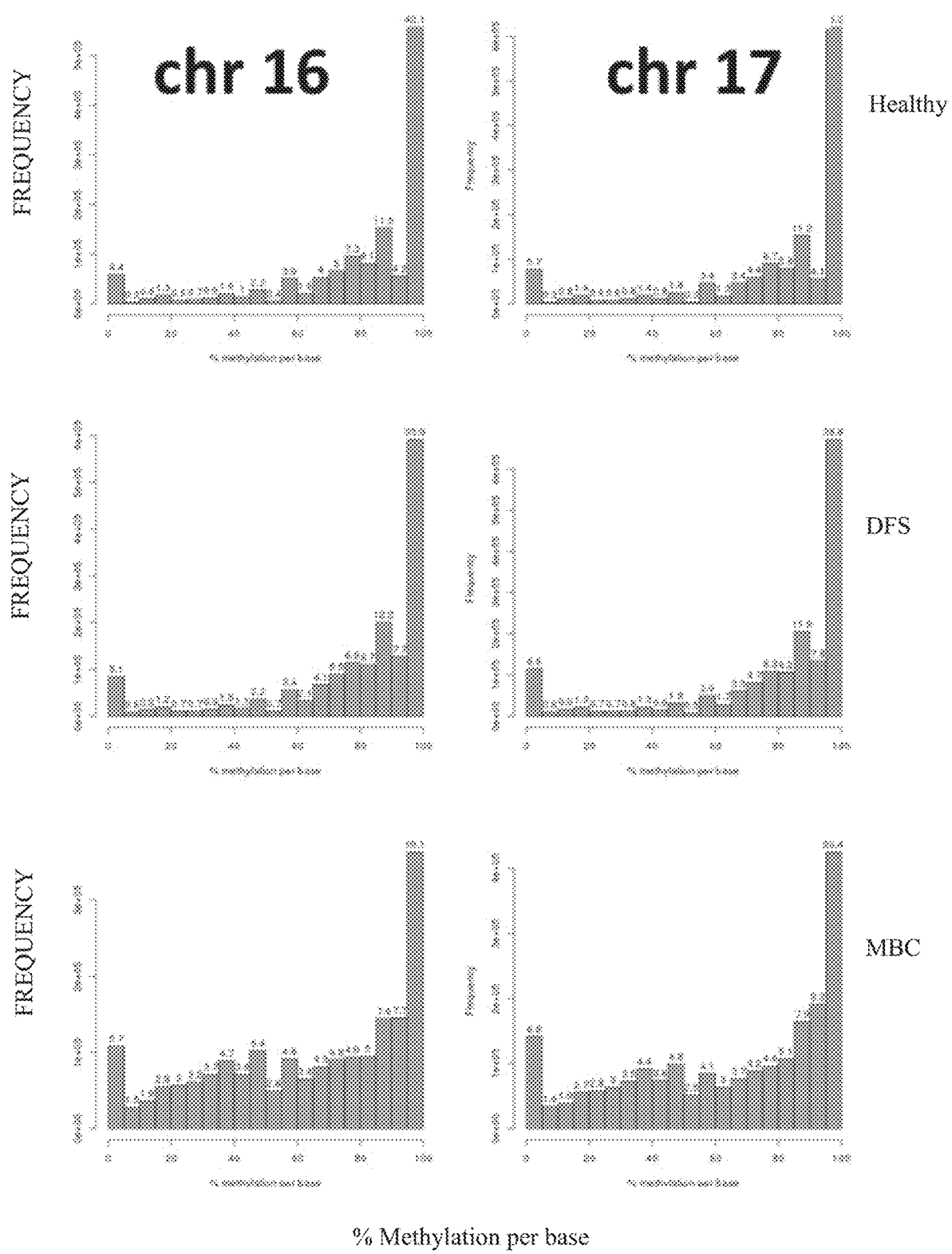
Figure 4:
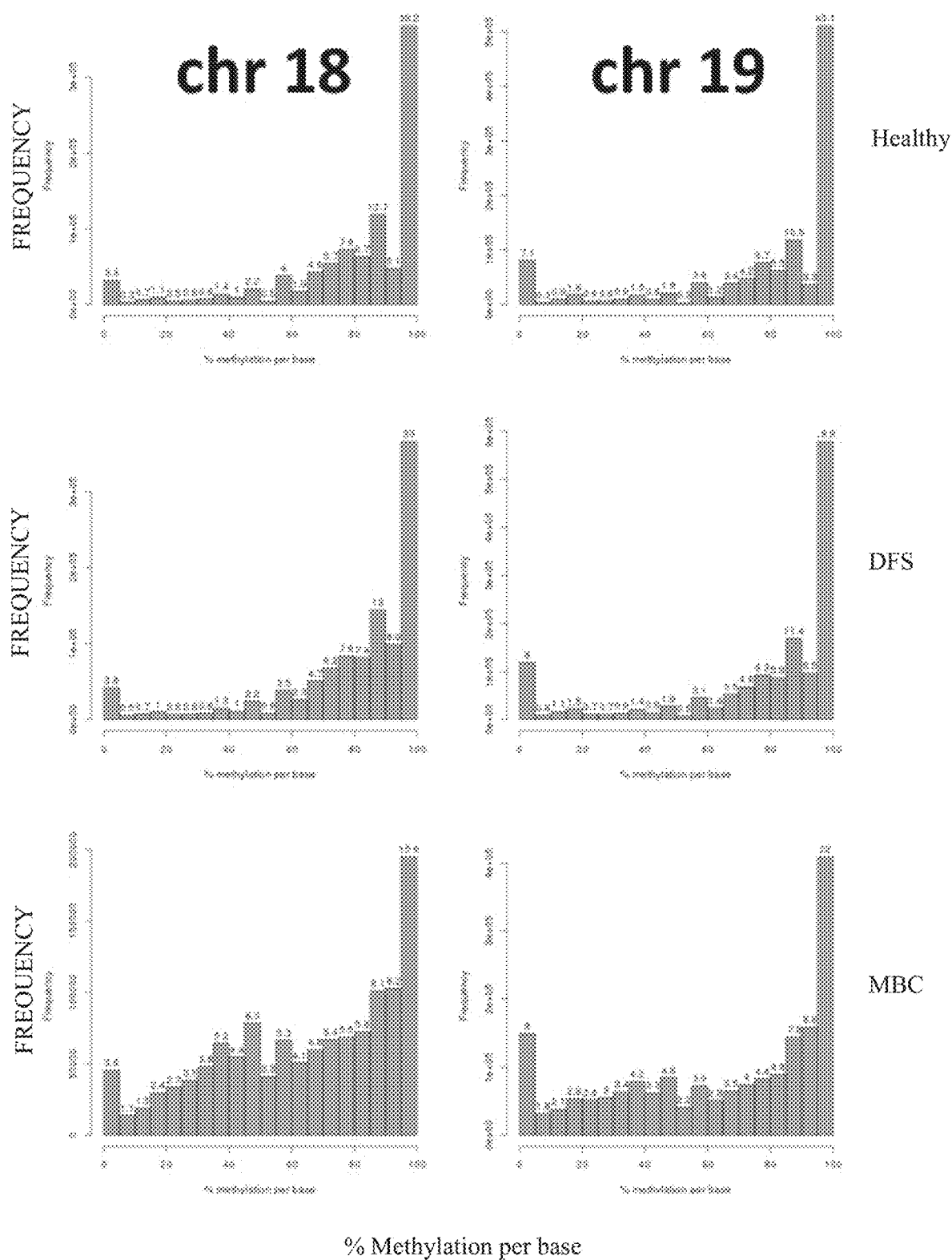
Figure 4:
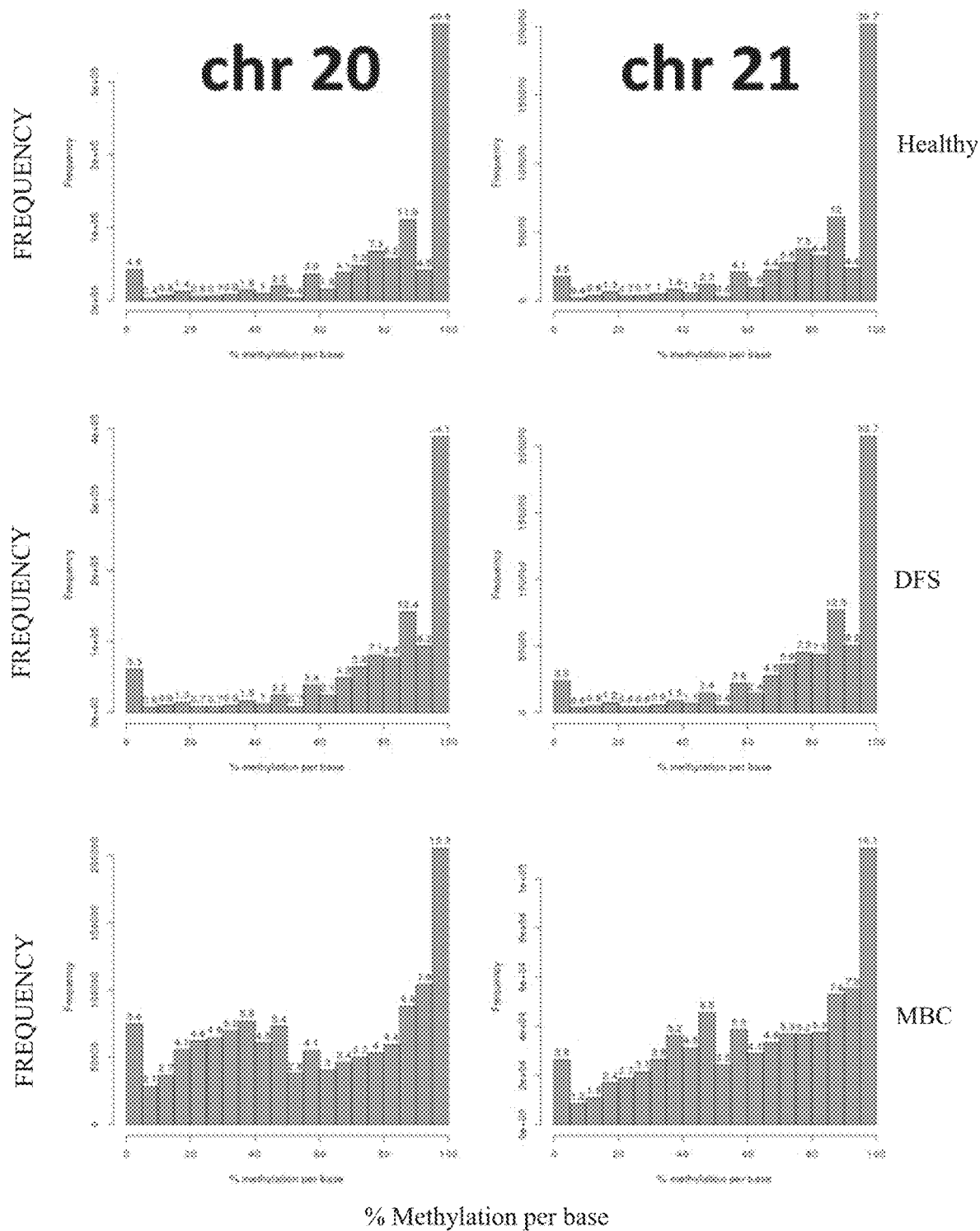
Figure 4:
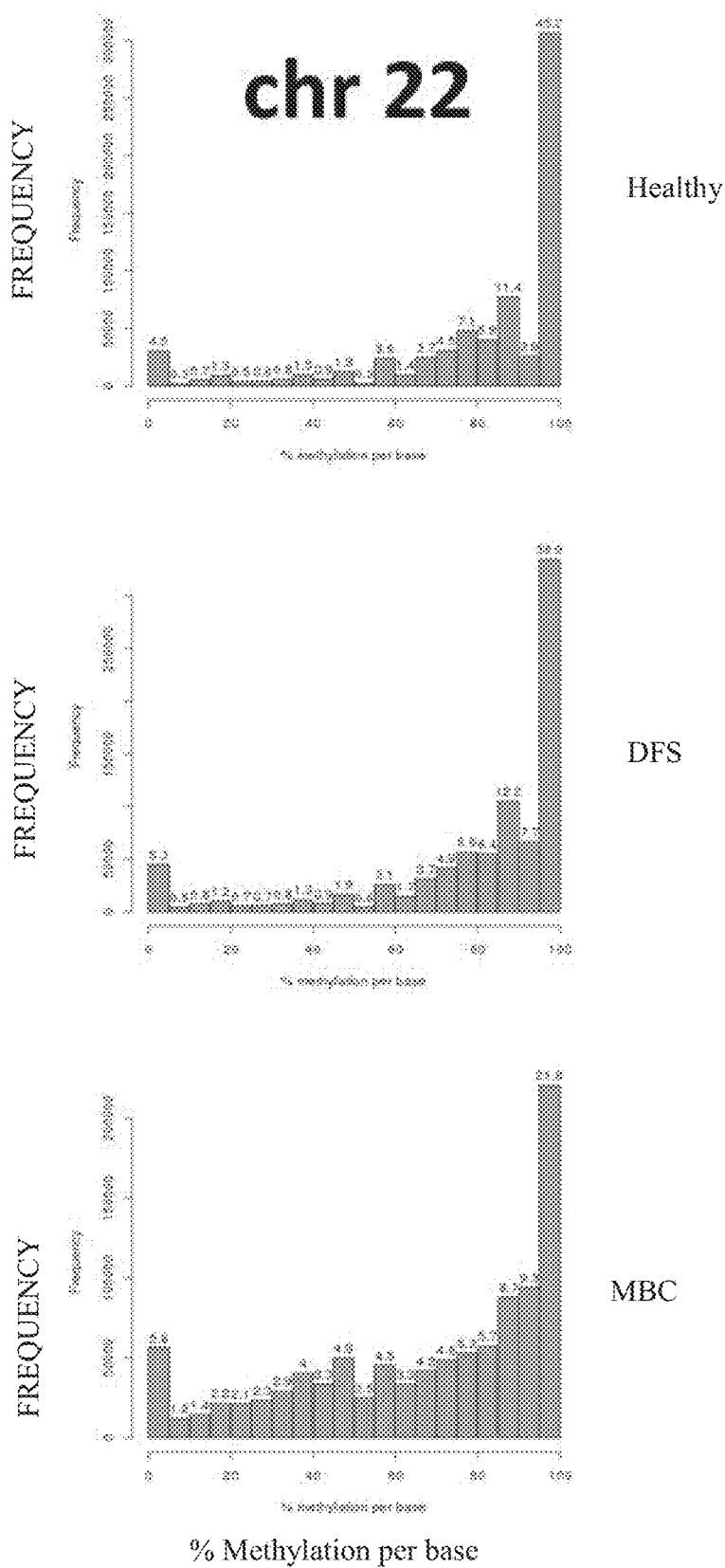

To assess the similarity of each sample group to the other we used methylKit to compute pair-wise Pearson correlation coefficients, hierarchical clustering (Ward's method, correlation distance metric) and Principal Component Analysis (PCA) on percent CpG methylation profiles. These analyses demonstrated that the H cohort closely resembled DFS, evidenced by Pearson correlation coefficient (0.83), and close proximity by hierarchical clustering and PCA. (FIGS. 3A, 3B, and 3C). However, MBC varied dramatically from H and DFS according to each analysis type, where the Pearson correlation coefficients were 0.57 and 0.59, and showed a large degree of separation by clustering and PCA. The percent methylation values per base for each sample group demonstrated that the majority of loci in DFS and H were methylated (major peak close to 1), whereas MBC had a significant proportion of loci shifted to the left indicating low methylation states and hypomethylation compared to H and DFS. To rule out a chromosomal bias we performed this analysis for each chromosome (excluding X and Y) and confirmed a similar trend (FIG. 4).

Figure 5:
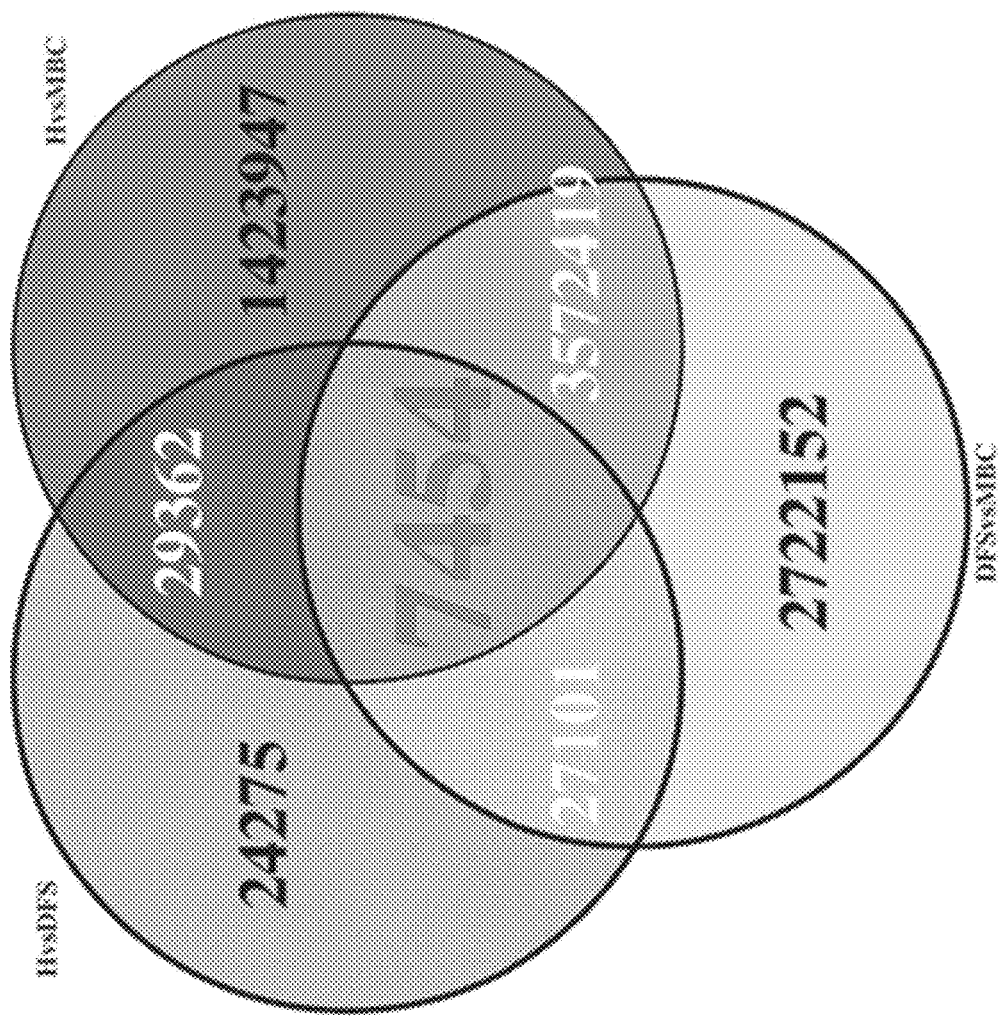
FIGS. 5A and 5B depict three pair-wise comparisons assessing cfDNA differential methylation between Healthy, DFS or MBC. A) Venn diagram showing the overlap of DML lists as generated by WGBS for H, DFS, and MBC sample comparisons. B) Three pair-wise comparisons assessing cfDNA differential methylation between H, DFS, and MBC. Pie charts show percentages of differentially hyper- or hypomethylated CpG loci genome-wide and within the displayed genomic contexts. Greater than 90% of CpG loci are hypomethylated genome-wide in MBC compared with Healthy or DFS. The majority of hypermethylated loci in MBC occur within CpG islands. The number of DML and the percentages are shown within each pie chart.
Figure 5:
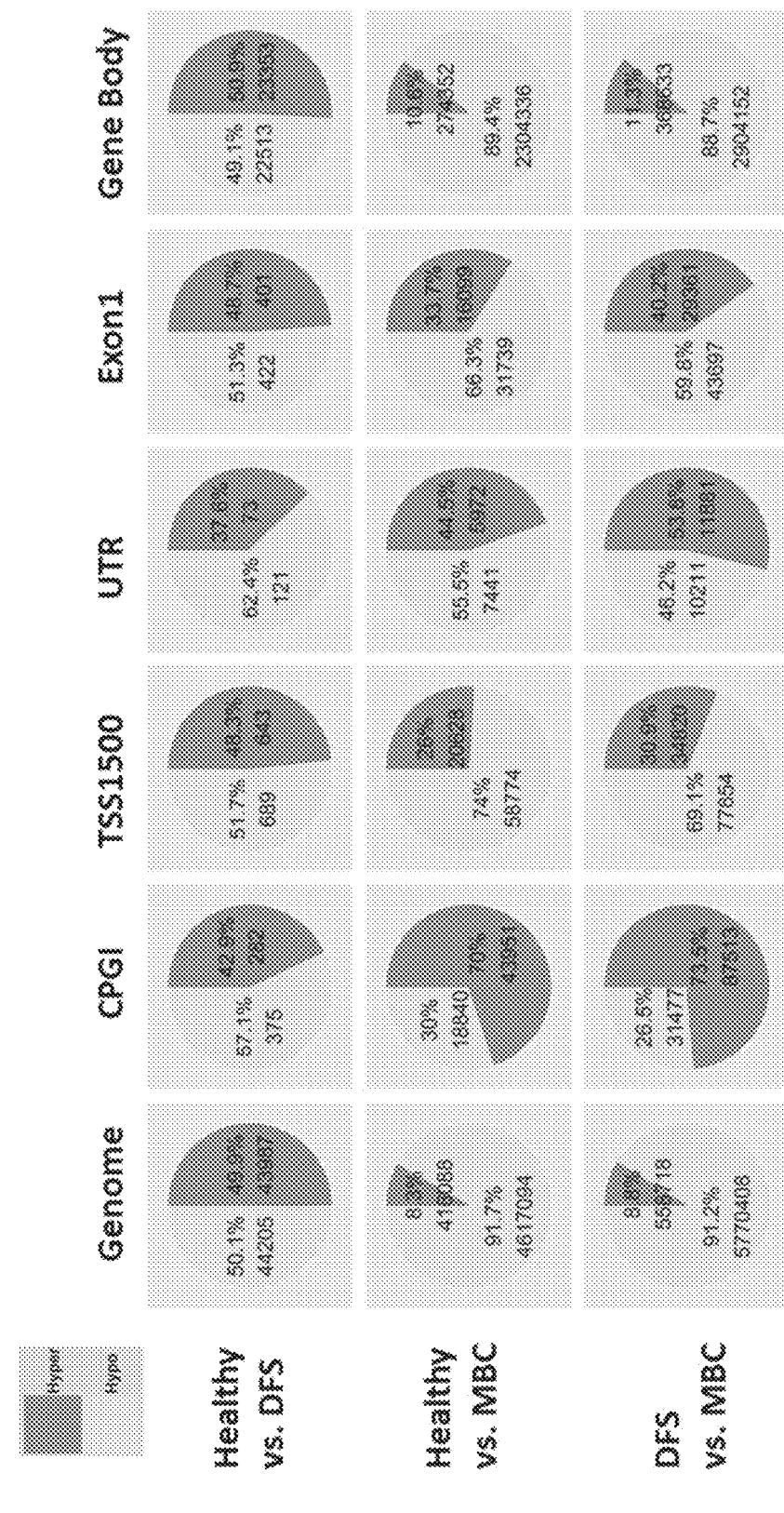

The investigators also used methylKit to perform pair-wise differential methylation analysis at a single base-pair level. The number of differentially methylated loci (DML) between H and DFS was relatively small (n=88,192), again indicating the similarity between the groups. In contrast, ~6.3×106 DML were detected between MBC and DFS and ~5.0×106 DML detected between MBC and H (FIG. 5A). A Venn diagram (FIG. 5A) showing the overlap of DML from each comparison demonstrates a high degree of overlap when MBC is compared to either H or DFS. However, very little overlap exists with the H vs. DFS DML list when compared to the DML list generated in the two MBC comparisons. Greater than 90% of DML were hypomethylated in MBC compared with either H or DFS, indicating genome-wide global hypomethylation in the plasma of MBC (FIG. 5B). To discern the biological impact of differentially methylated loci, each event was put into a genomic context: CpG island, TSS1500, UTR, Exon 1, and Gene Body (FIG. 5B). Approximately 9% of DML were hypermethylated in MEC compared to either H or DFS. The greatest number of hypermethylated DML occurred in CPGIs (~70%). There was also significant (P value<0.05) hypermethylation occurring in UTRs (~50%), Exon 1 (~35%), and TSS1500 (~30%). Hypermethylation occurred least frequently in gene bodies (~11%), which were predominately hypomethylated.

Figure 6A:
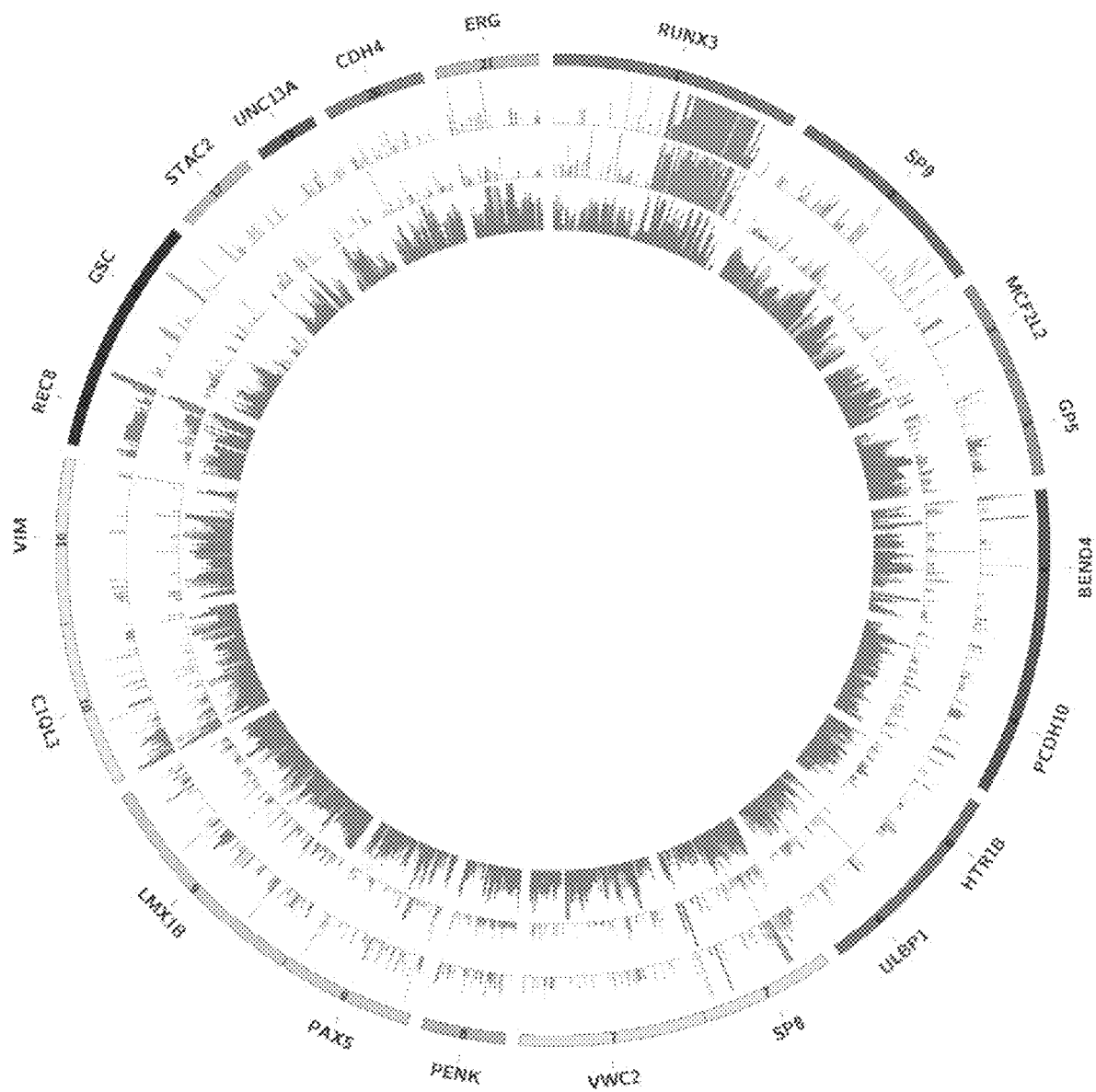
FIGS. 6A and 6B depict the results of mining for potential biomarkers of MBC. A) Circos plot graphing each locus belonging to the target CpG island for each of the 21 genes. Inner circle (red) is MBC, middle circle is DFS (green) and outer circle is H (blue). B) Vertical scatter plot showing all DML within target CPGIs of MBC. Each point represents a CpG locus. Points plotted on the x-axis display the DMV of MBC to DFS or Healthy.
Figure 6B:
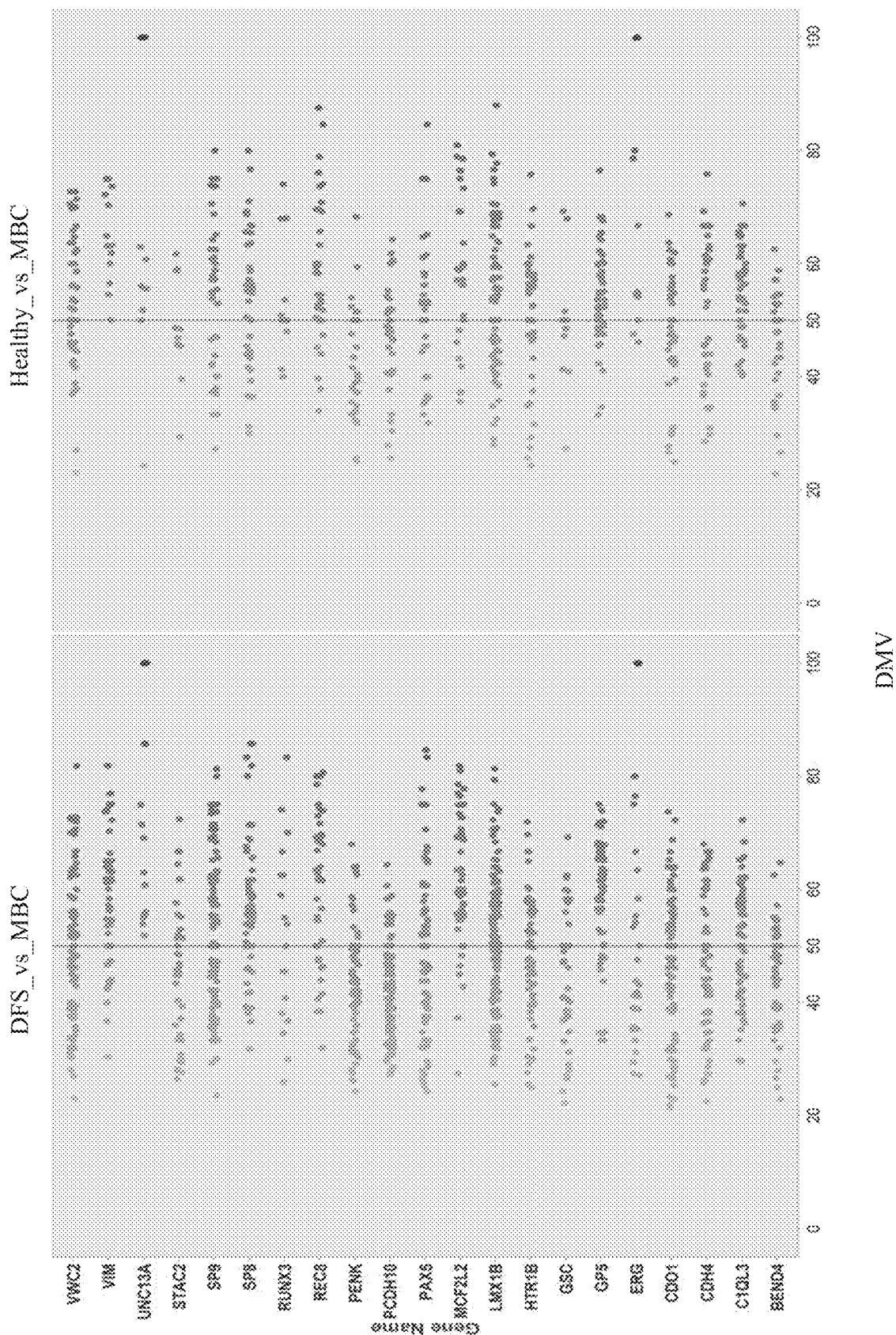

To mine the data for potential biomarkers of MBC, we focused on hypermethylated loci specifically in CPGIs because they tend to be focal in nature and were identified as the regions that differed most dramatically from normal or disease-free patterns. We specifically selected regions with eight or more hypermethylated loci with differential methylation values (DMVs)≥50. With these criteria, the investigators identified 21 CPGI hotspots, which are referred to as CpG4C™, within the following genes: BEND4, CDH4, C1QL3, ERG, GP5, GSC, HTR1B, LMX1B, MCF2L2, PAX5, PCDH10, PENK, REC8, RUNX3, SP8, SP9, STAC2, ULBP1, UNC13A, VIM, VWC2 (FIGS. 6A and 6B).

Figure 7A:
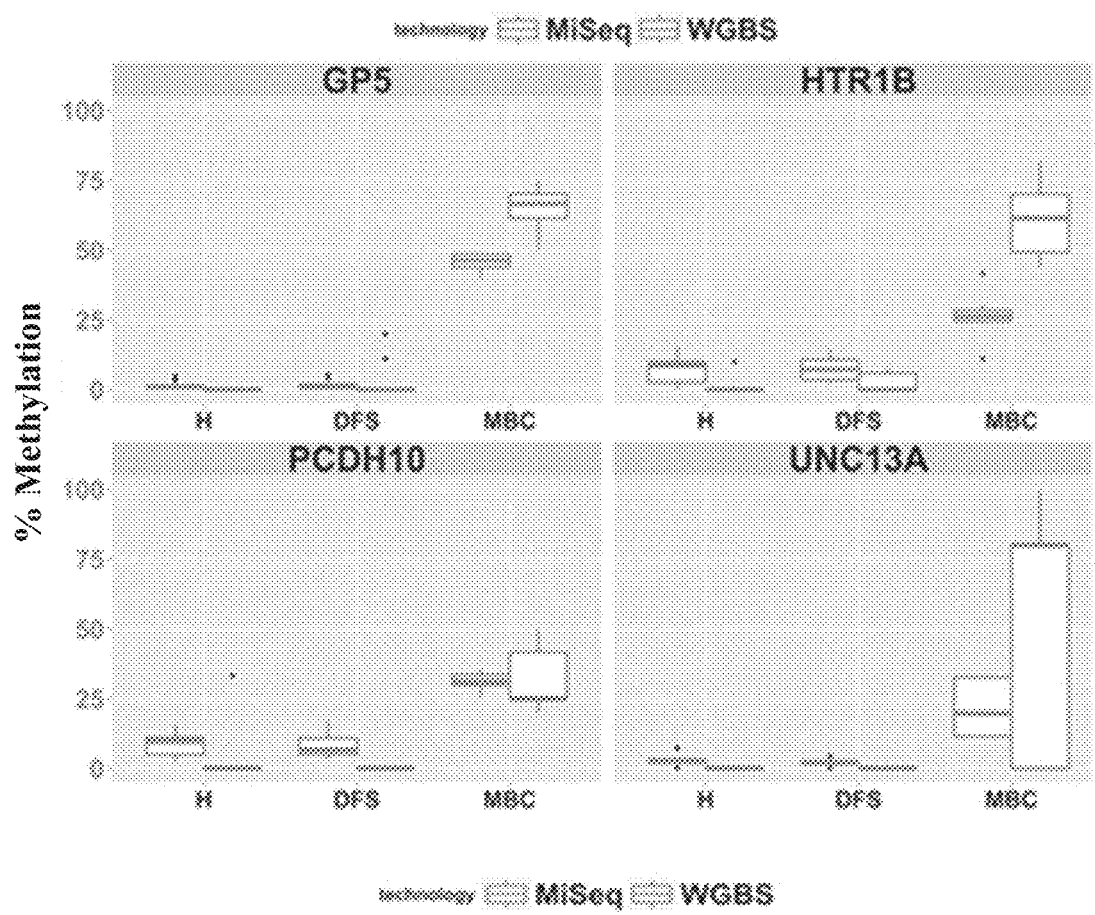
FIGS. 7A-7D depict comparisons of WGBS to MiSeq (targeted amplicon sequencing). A) Box plots representing percent methylation for DMLs in GP5, HTR1B, PCDH10, and UNC13A as called by both technologies. B) Mean-Whisker plots displaying average methylation state of all amplicons assayed by MiSeq and WGBS. C) Scatter plot of percent methylation value for the 36 CpGs assayed in H, DFS, and MBC by both MiSeq and WGBS. The correlation is reported as $R^2=0.768$. D) Pearson correlation coefficient for WGBS versus MiSeq for 36 CpGs assayed by targeted amplicon sequencing.
Figure 7B:
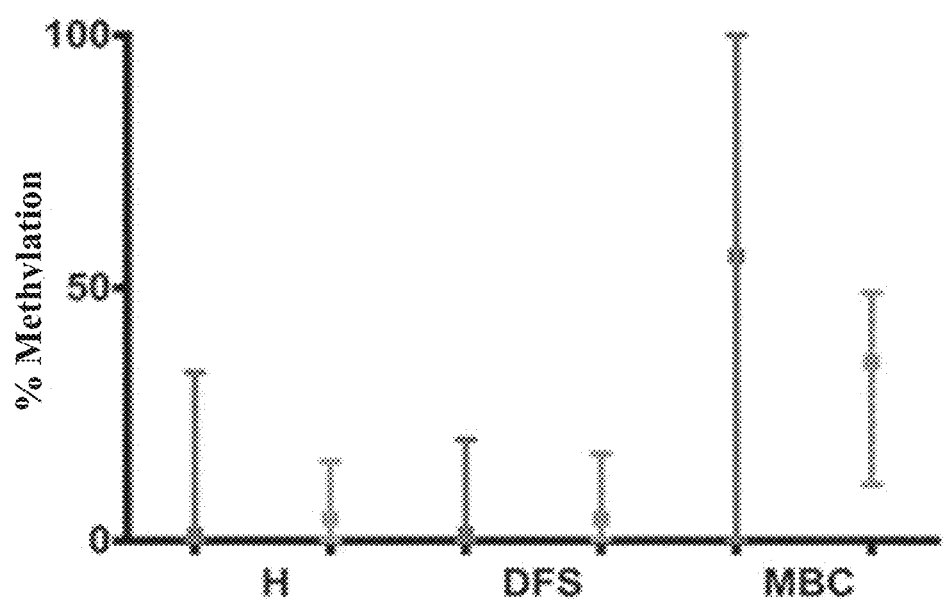
Figure 7C:
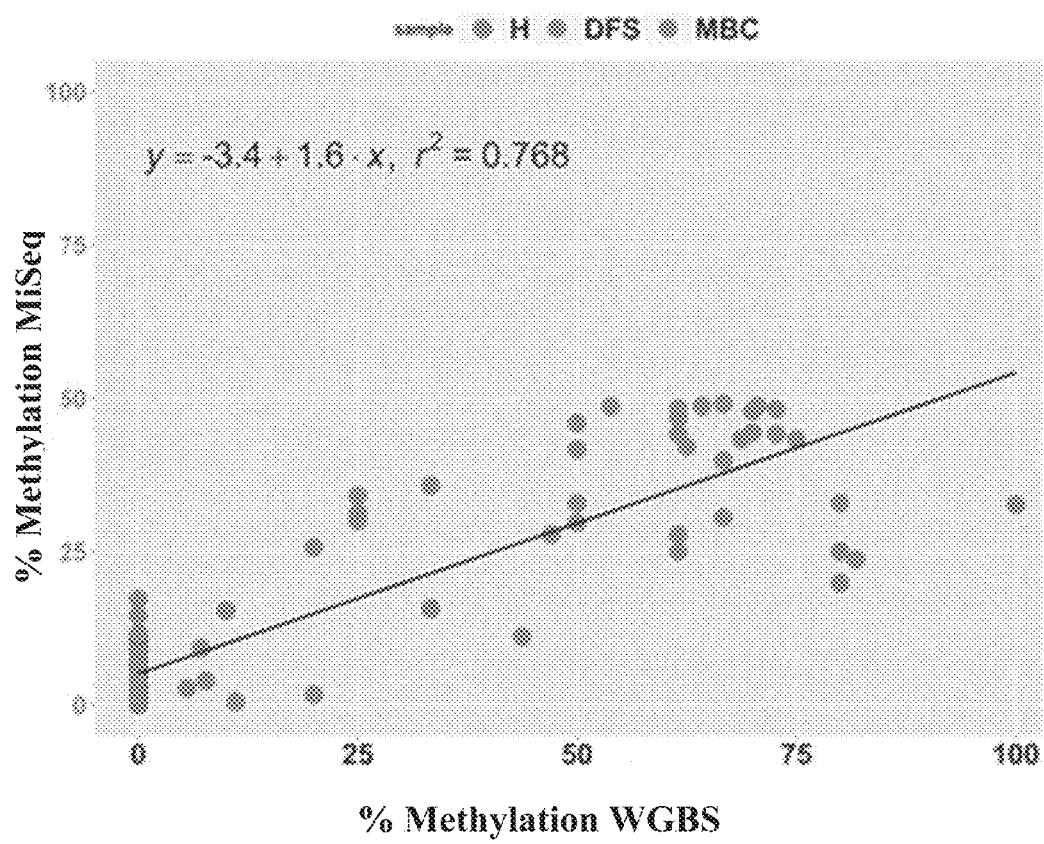
Figure 7D:
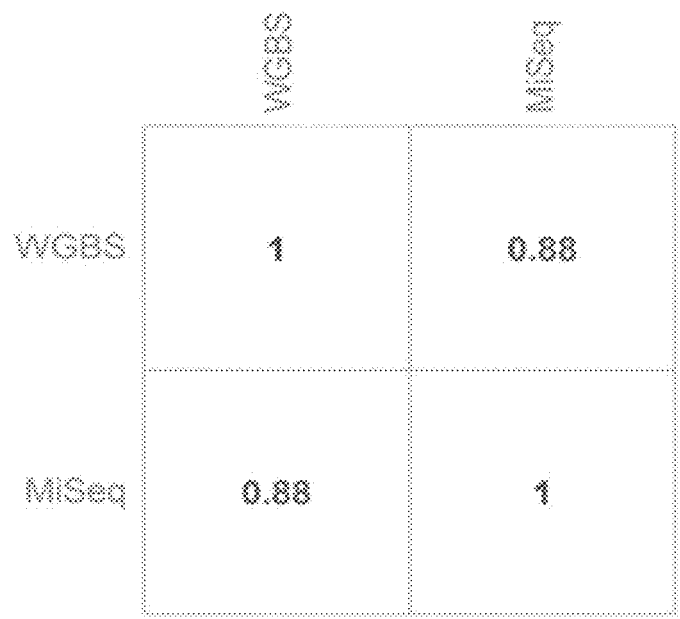

The investigators used bisulfite amplicon sequencing on Illumina's MiSeq platform for technical validation of WGBS on an independent extraction of plasma from each group. This nascent, deep-sequencing strategy allows for sensitive detection of DNA methylation in low-input samples such as plasma. The investigators randomly selected 4/21 genes for technical validation using MiSeq— the selected genes included GP5, UNC13A, PCDH10, and HTR1B genes and designed bisulfite PCR primers within the region of interest. Each amplicon detected between 6-18 CpG loci. Targeted bisulfite amplicon sequencing on the MiSeq platform showed very good concordance with WGBS and demonstrated statistically significant (P value<0.05) increased methylation in MBC compared with H and DFS in GP5, PCDH10, HRR1B, and UNC13A (FIGS. 7A and 7B). The MiSeq data also maintained that H and DFS are virtually unmethylated within these amplicons (FIGS. 7A and 7B). All comparisons between MBC and H or DFS were statistically significant (P value<0.05) by Fisher's Exact Test and ANOVA, while surviving multiple test correction (q value<0.5). To further assess the degree of correlation between MiSeq and WGBS data for the amplicons containing the 36 CpG assayed, we performed a scatter plot analysis and a Pearson correlation analysis to compare the 36 loci, for all groups, between the two technologies. This analysis demonstrated a high degree of correlation between MiSeq and WGBS ($R^2$=0.768 and Pearson Correlation=0.88) (FIGS. 7C and 7D. All loci in H and DFS (green and blue dots, respectively) clustered to very low methylation states to the lower left of the graph and CpG loci in MBC (red dots) mostly scattered to the upper right (FIG. 7C). A summary of the percent methylation values for each technology across the groups is shown in Table 3.

Supplementary Table 3.
Summary of Percent Methylation Values for WGBS and MiSeq for 36 CpG within GP5, HTR1B, PCDH10, and UNC13A

|  | H-WGBS | H-MiSeq | DFS-WGBS | DFS-MiSeq | MCB-WGBS | MCB-MiSeq |
|---|---|---|---|---|---|---|
| Number of Values | 36 | 36 | 36 | 36 | 36 | 36 |
| Minimum | 0 | 0 | 0 | 0.2132 | 0 | 11.11 |
| 25% Percentile | 0 | 0.692 | 0 | 0.9827 | 47.79 | 27.78 |
| Median | 0 | 2.665 | 0 | 2.824 | 61.54 | 34.94 |
| 75% Percentile | 0 | 8.178 | 0 | 6.353 | 70.44 | 45.54 |
| Maximum | 33.33 | 15.69 | 20 | 17.24 | 100 | 49.11 |
| Mean | 1.204 | 4.402 | 1.431 | 4.354 | 56.36 | 35.38 |
| Std. Deviation | 5.754 | 4.468 | 4.109 | 4.377 | 22.65 | 11.43 |
| Std. Error of Mean | 0.9591 | 0.7447 | 0.6848 | 0.7295 | 3.776 | 1.906 |

-continued

Supplementary Table 3.
Summary of Percent Methylation Values for WGBS and MiSeq for
36 CpG within GP5, HTR1B, PCDH10, and UNC13A

|  | H-WGBS | H-MiSeq | DFS-WGBS | DFS-MiSeq | MCB-WGBS | MCB-MiSeq |
|---|---|---|---|---|---|---|
| Lower 95% CI of mean | −0.7433 | 2.89 | 0.04044 | 2.873 | 48.7 | 31.52 |
| Upper 95% CI of mean | 3.151 | 5.914 | 2.821 | 5.835 | 64.03 | 39.25 |

Figure 8:
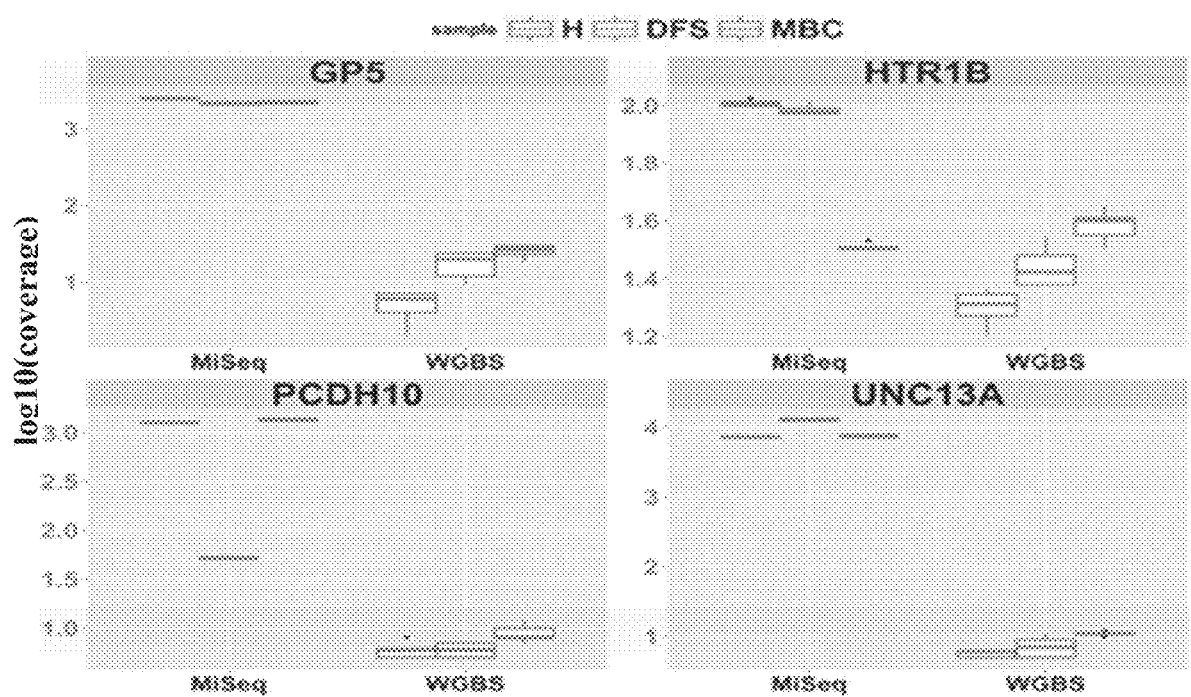
FIG. 8 depicts read coverage in DMLs of interest. Box plots show the depth of sequencing as determined by WGBS and MiSeq for 36 DMLs specific to GP5, HTR1B, PCDH10, and UNC13A in all pools of H (blue), DFS (green), and MBC (red). Coverage is shown as log 10.

To demonstrate the expected higher coverage of MiSeq with WGBS, the investigators calculated the mean depth of coverage for each CpG locus, within each amplicon, for each group (FIG. 8). The overall average depth of coverage for the 36 CpG loci in H, DFS, and MBC by WGBS was 10, 9.4, and 11. The average number of reads for H, DFS, and MBC by MiSeq was 3012, 2583, and 2516, respectively.

In order to demonstrate the association of the 21 gene panel to biological processes we performed the Core Analysis in Ingenuity® Pathway Analysis (IPA®). The top disease implication was Cancer showing involvement of 17/21 genes (Table 4A). The Top Molecular and Cellular Function was Cell-Cell Signaling and Interaction (Table 4A). Within the Cancer disease process, 17 genes were associated with Digestive System Cancer (Table 4B). VIM and CDH4 were implicated in invasive cancer (Table 4B).

TABLE 4A

Ingenuity Pathway Analysis for 21 Gene Signature

| Name | P-Value Range | # Molecules |
|---|---|---|
| Top Diseases and Bio Functions Diseases and Disorders | | |
| Cancer | 4.7E-02-1.02E-03 | 17 |
| Dermatological Diseases and Conditions | 1.53E-02-1.02E-03 | 3 |
| Developmental Disorder | 4.41E-02-1.02E-03 | 7 |
| Endocrine System Disorders | 4.09E-02-1.02E-03 | 2 |
| Hematological Disease | 4.7E-02-1.02E-03 | 5 |
| Molecular and Cellular Functions | | |
| Cell-To-Cell Signaling and Interaction | 4.90E-02-1.13E-04 | 10 |
| Cell Morphology | 4.61E-02-2.59E-04 | 6 |
| Cellular Development | 5.00E-02-2.59E-04 | 13 |
| Cell Death and Survival | 4.41E-02-1.02E-03 | 6 |
| Cellular Assembly and Organization | 4.02E-02-1.02E-03 | 10 |

TABLE 4B

Detailed View of 17 Genes in Cancer as shown in Table 4A

| Categories | Diseases or Functions Annotation | p-Value | Molecules | # Molecules |
|---|---|---|---|---|
| Cancer, Endocrine System Disorders, Organismal Injury and Abnormalities, Tumor Morphology | invasion of papillary thyroid carcinoma | 1.02E-03 | VIM | 1 |
| Cancer, Endocrine System Disorders, Organismal Injury and Abnormalities | Metastasis of papillary thyroid carcinoma | 1.02E-03 | VIM | 1 |
| Cancer, Hematological Disease, Hereditary Disorder, Immunological Disease, Organismal Injury and Abnormalities | Susceptibility to acute lymphoblastic leukemia type 3 | 1.02E-03 | PAX5 | 1 |
| Cancer, Cardiovascular Disease, Dermatological Diseases and Conditions, Hereditary Disorder, Organismal Injury and Abnormalities | Carney complex type 1 | 2.05E-03 | VIM | 1 |
| Cancer, Hematological Disease, Immunological Disease, Organismal Injury and Abnormalities | Philadelphia-positive B-cell acute lymphoblastic leukemia | 2.05E-03 | PAX5 | 1 |
| Cancer, Hematological Disease, Immunological Disease, Organismal Injury and Abnormalities | Precursor T-cell lymphoblastic leukemia-lymphoma | 3.79E-03 | ERG, PAX5 | 2 |
| Cancer, Endocrine System | Invasive papillary | 4.09E-03 | VIM | 1 |

TABLE 4B-continued

Detailed View of 17 Genes in Cancer as shown in Table 4A

| Categories | Diseases or Functions Annotation | p-Value | Molecules | # Molecules |
|---|---|---|---|---|
| Disorders, Organismal Injury and Abnormalities | thyroid carcinoma | | | |
| Cancer, Cellular Growth and Proliferation, Organismal Functions, Organismal Injury and Abnormalities, Tumor Morphology | Inhibition of mammary tumor cells | 5.11E−03 | RUNX3 | 1 |
| Cancer, Organismal Injury and Abnormalities | Invasive adenocarcinoma | 5.21E−03 | CDH4, VIM | 2 |
| Cancer, Organismal Injury and Abnormalities | Tumorigenesis of stomach cancer cell lines | 6.13E−03 | RUNX3 | 1 |
| Cancer, Hematological Disease, Hereditary Disorder, Immunological Disease, Organismal Injury and Abnormalities | Philadelphia-negative B-cell acute lymphoblastic leukemia | 7.15E−03 | PAX5 | 1 |
| Cancer, Gastrointestinal Disease, Organismal Injury and Abnormalities | Digestive System Caner | 7.63E−03 | BEND4, C1QL3, CDH4, ERG, GP5, HTR1B, LMX1B, MCF2L2, PAX5, PCDH10, PENK, RUNX3, SP8, SP9, UNC13A, VIM, VWC2 | 17 |
| Cancer, Gastrointestinal Disease, Organismal Injury and Abnormalities | Hyperplasia of gastric epithelium | 8.16E−03 | RUNX3 | 1 |
| Cancer, Hematological Disease, Hereditary Disorder, Immunological Disease, Organismal Injury and | Type M7 acute myeloid leukemia | 9.18E−03 | ERG | 1 |
| Cancer, Cellular Development, Organismal Injury and Abnormalities | Immortalization of hematopoietic progenitor cells | 1.63E−02 | ERG | 1 |
| Cancer, Organismal Injury and Abnormalities | Invasive cancer | 1.76E−02 | CDH4, VIM | 2 |
| Cancer, Gastrointestinal Disease, Organismal Injury and Abnormalities | Colorectal adenocarcinoma | 2.13E−02 | CDH4, ERG, GP5, MCF2L2, PAX5, SP8, SP9, UNC13A, VIM, WC2 | 10 |
| Cancer, Gastrointestinal Disease, Organismal Injury and Abnormalities | Colorectal cancer | 2.55E−02 | CDH4, ERG, GP5, MCF2L2, PAX5, RUNX3, SP8, SP9, UNC13A, VIM, WC2 | 11 |
| Cancer, Gastrointestinal Disease, Organismal Injury and Abnormalities | Gastrointestinal adenocarcinoma | 2.61E−02 | CDH4, ERG, GP5, MCF2L2, PAX5, PCDH10, SP8, SP9, UNC13A, VIM, WC2 | 11 |
| Cancer, Gastrointestinal Disease, Hepatic System Disease, Organismal Injury and Abnormalities | Hepatobiliary system cancer | 2.91E−02 | BEND4, C1QL3, CDH4, ERG, GP5, HTR1B, LMX1B, PCDH10, PENK, UNC13A, VIM | 11 |
| Cancer, Hematological Disease, Immunological Disease, Organismal Injury and Abnormalities | Lymphocytic leukemia | 3.32E−02 | ERG, PAX5, PCDH10 | 3 |
| Cancer, Gastrointestinal Disease, Organismal Injury and Abnormalities | Gastrointestinal tract cancer | 3.48E−02 | CDH4, ERG, GP5, MCF2L2, PAX5, RUNX3, PCDH10, SP8, SP9, UNC13A, VIM, WC2 | 12 |

TABLE 4B-continued

Detailed View of 17 Genes in Cancer as shown in Table 4A

| Categories | Diseases or Functions Annotation | p-Value | Molecules | # Molecules |
| --- | --- | --- | --- | --- |
| Cancer, Cellular Development, Cellular Growth and proliferation, Organismal Injury and Abnormalities, Tumor Morphology | Colony Formation of cancer cells | 3.62E−02 | RUNX3 | 1 |
| Cancer, Organismal Injury and Abnormalities | Ductal carcinoma | 3.75E−02 | CDH4, RUNX3 | 2 |
| Cancer, Gastrointestinal Disease, Organismal Injury and Abnormalities | Rectal adenocarcinoma | 4.32E−02 | PAX5, SP9, WC2 | 3 |
| Cancer, Hematological Disease, Immunological Disease, Organismal Injury and Abnormalities | Precursor B-cell acute lymphoblastic leukemia | 4.71E−02 | PAX5 | 1 |

In summary, cancer metastases arise from disseminated cells of the primary tumor mass before treatment and/or from minimal residual disease (MRD) persisting after therapy (collectively known as micrometastatic residual disease). Currently, there are no effective methods to determine which patients harbor micrometastatic disease after standard breast cancer therapy and who will eventually develop local or distant recurrence. It would be advantageous to determine the subset of patients who harbor micrometastatic cells, and develop trials that would evaluate the use of additional therapy for eventual prevention of metastasis. There is likely a predictive clinical window of opportunity to detect microscopic disease in the early disease setting before micrometastases lead to incurable macrometastases, years after initial diagnosis. While other studies have reported the detection of tumor-associated DNA methylation changes in cfDNA, targets were usually selected a-priori from tissue microarray data and measured using targeted approaches. This study represents an unbiased whole-genome approach for discovery of circulating biomarkers directly implicating 21 genic hotspots, for the first time, in the circulation of MBC patients. The investigators anticipate that this 21 DNA hypermethylation signature of rationally selected CpG hotspots, detectable in circulation, can be used to indicate micrometastatic disease in the pre-macrometastatic setting, and predict patients at high-risk of recurrence who could benefit from additional therapy. Studies are ongoing to validate these findings using bisulfite amplicon sequencing in both the current and pre-metastatic cohorts in order to determine the specificity and sensitivity to predict recurrence and to determine utility across different BC subtypes.

Materials and Method

Sample Acquisition and DNA Extraction

The investigators obtained 120 retrospectively collected plasma samples from the Komen Tissue Bank (KTB), IU Simon Cancer Center representing 3 cohorts of 40 individuals: cohort 1 is MBC to various organs; cohort 2 is DFS (range: 3-27 years, average 9 years DFS); cohort 3 is H with no history of cancer. Samples were obtained under informed consent following Komen Tissue Bank Institutional Review Board approval. Plasma collection and processing is critical to the reproducibility of tests involving cfDNA. The KTB uses a highly standardized and meticulous protocol for processing plasma to ensure separation from blood and subsequent storage in a highly time efficient manner. A plasma pool for each cohort was created by mixing 50 µl of a pre-aliquoted plasma sample per individual, followed by extraction of cfDNA from 1 ml of each pool using the QIAamp DNA Micro Kit (Qiagen) according to the manufacturer's protocol, with the exception that we used 1 µg of carrier RNA. DNA yields from four independent 1-ml extractions of each pool were highly consistent. The manufacturer's protocol for "Isolation of Genomic DNA from Small Volumes of Blood" was followed, with the exception that reagents were scaled up proportionally, and the sample was serially extracted on the column to accommodate the increased volume. DNA was eluted in AE Buffer (Qiagen) and quantified using the Qubit dsDNA High Sensitivity fluorometric assay (Invitrogen).

DNA Methylation Analysis by Whole-Genome Bisulfite Sequencing

Directional bisulfite-converted libraries for paired-end sequencing were prepared using the Ovation Ultralow Methyl-Seq Library System (NuGen). The manufacturer's suggested protocol was followed. Briefly, this entailed fragmentation, end repair, adapter ligation, final repair, bisulfite conversion, and PCR amplification. The investigators used 27, 14, and 33 ng of DNA for H, DFS, and MBC, respectively, in 50 µl T low E buffer, which was fragmented to an average size of 200 bp using the Covaris S2 system. Bisulfite conversion was performed using the EpiTect Fast DNA Bisulfite Kit (Qiagen) as per manufacturer's instructions. Post-library QC was performed with BioAnalyzer DNA 1000 chips (Agilent) and the Qubit dsDNA High Sensitivity fluorometric assay (Invitrogen). An equimolar pool of the prepared libraries was created at a concentration of 5 nM. The sample was subsequently diluted and clustered on the Illumina cBot using TruSeq Paired End Cluster Kit v.3 chemistry. Paired-end sequencing was performed on the Illumina HiSeq 2500 platform using TruSeq SBS v3 kits for a total read length of 200 bp.

Targeted Bisulfite Amplicon Sequencing

Targeted bisulfite amplicon sequencing was performed on the MiSeq (Illumina) using an independent replicate of the three plasma pools for validation of CpG island hotspots for GP5, HTR1B, PCDH10, UNC13A. Bisulfite Primer Seeker 12S (Zymo Research) was used to create primer-pairs specific for bisulfite-converted DNA, which produced PCR amplicons ranging in size from 109-235 base pairs. The bisulfite conversion was accomplished using EZ DNA Methylation-Gold Kit (Zymo Research) according to the manufacturer's standard protocol. Forty cycle PCR reactions were carried out with the Zymo Taq (Zymo Research) kit and the manufacturer's recommended conditions using 2 µl of converted DNA template per 30 µl reaction. Reactions were purified using NucleoSpin columns (Macherey-Nagel) as per the manufacturer's suggested protocol. Purified reaction products were run out on a 2% agarose gel for visual inspection and quantified using the Qubit dsDNA High Sensitivity fluorometric assay (Invitrogen).

A 266-ng equimolar mix of the four amplicons was used as input for sequencing library preparation using the Kapa Hyper Prep Kit (Kapa Biosystems). TruSeq DNA LT adapters (Illumina) were used for indexing. No post-ligation amplification was performed. Quantitative-PCR library quantification was carried out using the Kapa Library Quantification Kit (Kapa Biosystems).

Equimolar library pools were created and diluted to 15 pM for denaturation. PhiX Control v3 (Illumina) was spiked in at a 5.0% final concentration, and subsequent cluster generation/sequencing was performed on the MiSeq using MiSeq Reagent Nano Kits (Illumina). Five hundred cycles of 2×250 paired-end sequencing generated over 820,000 reads.

Data Processing and Analysis

Bisulfite-modified DNA reads from WGBS and MiSeq were aligned to the bowtie2-indexed reference genome GRCh37-62 using Bismark tool version 0.12.7. Bismark relies on two external tools, bowtie and Samtools. The investigators respectively used bowtie2 version 2.0.0-beta6, and Samtools version 0.1.19. Bismark was used as suggested except for the bowtie2's parameter N (number of mismatches in a seed alignment during multispeed alignment) where the value of 1 was used for increased sensitivity. Next, PCR duplicates were removed for WGBS using default parameters. Methylation calling was also processed using a Bismark module called "Methylation Extractor," which was used according to the author's specifications. Base-pair level differential methylation analysis was implemented using the R package methylKit 0.9.2. Bismark's sam file output was used as input to methylKit and data imported using the embedded function "read.bismark". The minimum read coverage to call a methylation status for a base was set to 5, and the minimum phred quality score to call a methylation was set to 20. The read.context option was set to "CpG". Other options to the read.bismark function were set to default values. The following pair-wise comparisons were performed in methylKit using the Fisher Exact Test: H versus DFS, H versus MBC, and DFS versus MBC for both WGBS and MiSeq datasets. Before calling differential methylation, each comparison was methylKit-reorganized, united, and then underwent differential methylation analysis using methylKit functions. With a minimum of five reads in each group, a differential methylation value (DMV) of 20 (in percent scale) and P values<0.05 were considered DML. For WGBS and MiSeq, chromosome X and Y reads were removed. MethylKit DML calls were annotated according to genomic location: Exon 1, Gene Body, TSS1500, UTR5-prime, and CPGI annotations. For selection of biomarkers, we identified CPGIs with at least 8 DML having DMVs greater than 50. All loci of interest were visually inspected in Integrated Genomic Viewer (IGV). The investigators hereby incorporate by reference for all purposes the following article: C. Legendre et al., *Whole Genome Bisulfate Sequencing of Cell-Free DNA Identifies Signature Associated with Metastatic Breast Cancer*, Clinical Epigentics 7:100 2015.

Unless defined otherwise, all technical and scientific terms herein have the same meaning as commonly understood by one of ordinary skill in the art to which this technology belongs. Although any methods and materials, similar or equivalent to those described herein, can be used in the practice or testing of the present technology, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present technology is not entitled to antedate such publication by virtue of prior technology.

While the technology has been described in connection with specific embodiments thereof, it will be understood that it is capable of further modifications and this application is intended to cover any variations, uses, or adaptations of the technology following, in general, the principles of the technology and including such departures from the present disclosure as come within known or customary practice within the art to which the technology pertains and as may be applied to the essential features hereinbefore set forth and as follows in the scope of the appended claims.

The invention claimed is:

1. A method for diagnosing and treating micrometastatic residual disease in a subject with breast cancer, the method comprising the steps of:
   a) determining a methylation level of GP5 in nucleic acids extracted from a cell-free sample from the subject with breast cancer;
   b) comparing the subject-derived methylation level of GP5 as determined in step a) with a normal control methylation level of GP5 in nucleic acids extracted from normal cell-free samples;
   c) diagnosing the subject with breast cancer as having micrometastatic residual disease by detecting an increase of said subject-derived methylation level of GP5, as compared to the normal control methylation level of GP5; and
   d) administering to the subject with breast cancer and diagnosed as having micrometastatic residual disease in step c, a compound selected from the group consisting of: Vidaza, decitabine, Entinostat, a PARP inhibitor, and combinations thereof.

2. The method of claim 1, wherein the methylation level is determined by whole genome bisulfate sequencing.

3. The method of claim 1, wherein the methylation level is determined using a method selected from the group comprising bisulfite treatment of DNA, whole genome bisulfite sequencing (WGBS), reverse phase high pressure liquid chromatography (HPLC), methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, methylation detection after restriction, methylation-sensitive restriction fingerprinting, restriction landmark genomic scanning (RLGS), or bisulfite conversion combined with bisulfite restriction analysis (COBRA).

4. The method of claim 1, wherein the nucleic acids are DNA.

5. The method of claim 1, wherein the cell-free sample is one of plasma and serum.

6. The method according to claim 1, further comprising:
e) determining a methylation level of HTR1B, PCDH10, and UNC13A, in the nucleic acids extracted from the cell-free sample from the subject with breast cancer;
f) comparing the subject-derived methylation level of HTR1B, PCDH10, and UNC13A as determined in step e) with a normal control methylation level of HTR1B, PCDH10, and UNC13A in nucleic acids extracted from normal cell-free samples; and
g) confirming a diagnosis of the subject with breast cancer as having micrometastatic residual disease by detecting an increase of said subject-derived methylation level of at least one of HTR1B, PCDH10, and UNC13A, as compared to the normal control methylation level of HTR1B, PCDH10, and UNC13A.

7. The method according to claim 6, further comprising:
h) predicting a cancer type of the micrometastatic residual disease in the subject with breast cancer and diagnosed as having micrometastatic residual disease by detecting an increase of said subject-derived methylation level of GP5, HTR1B, PCDH10, and UNCI3A, compared to the normal control methylation level of GP5, HTR1B, PCDH10, and UNC13A
wherein the cancer type is digestive system cancer.

* * * * *